United States Patent [19]
Hakomori et al.

[11] Patent Number: 5,272,138
[45] Date of Patent: Dec. 21, 1993

[54] NATURALLY OCCURRING GANGLIOSIDES CONTAINING DE-N-ACETYL-SIALIC ACID AND THEIR APPLICATIONS AS MODIFIERS OF CELL PHYSIOLOGY

[75] Inventors: Sen-itiroh Hakomori; Gustavo A. Nores; Nobuo Hanai; Taeko Dohi; Steven B. Levery; Mary Ellen K. Salyan; Hisao Nojiri, all of Seattle, Wash.

[73] Assignee: The Biomembrane Institute, Seattle, Wash.

[21] Appl. No.: 467,458

[22] Filed: Jan. 19, 1990

Related U.S. Application Data

[63] Continuation-in-part of Ser. No. 232,219, Aug. 15, 1988, abandoned, which is a continuation-in-part of Ser. No. 303,211, Jan. 30, 1989, abandoned, which is a continuation-in-part of Ser. No. 155,401, Feb. 12, 1988, abandoned.

[51] Int. Cl.$^5$ .............. A61K 31/70; A61K 31/725; C07H 5/06; C07H 13/06
[52] U.S. Cl. .................. 514/61; 514/25; 514/54; 514/62
[58] Field of Search ............ 536/4.1, 53, 55.1, 55.3; 514/25, 53, 54, 62, 61

[56] References Cited

U.S. PATENT DOCUMENTS 4,918,170 4/1990 Hasegawa et al. ............ 536/1.1
4,968,786 11/1990 Ogawa et al. ............ 536/17.9

OTHER PUBLICATIONS

Higashi et al; Analytical Biochemistry 120: 159–164 (1982).
Bremer et al; Journal of Biological Chemistry 259(11):6818–6825 (1984).
Bremer et al; Journal of Biological Chemistry 261(5):2434–2440 (1986).
Hanai et al; Biochemical and Biophysical Research Communications 147(1):127–134 (Aug. 31, 1987).
Meuenhofer et al; Biochemistry 24:525–532 (1985).

*Primary Examiner*—Nancy S. Husarik
*Attorney, Agent, or Firm*—Sughrue, Mion, Zinn, Macpeak & Seas

[57] ABSTRACT

A method for preparing de-N-acylated forms of an N-acyl sugar-containing glycosphingolipid and lyso forms of glycosphingolipid comprising hydrolyzing the glycosphingolipids under mild alkaline conditions such that the N-acyl group of the sugar moiety is preferentially hydrolyzed. Substantially pure gangliosides containing de-N-acetyl-sialic acid isolated from natural sources. A culture medium for stimulating growth of human and animal cells comprising: essential nutrients for cell growth, and a cell growth stimulatory amount of one or more gangliosides containing de-N-acetyl-sialic acid. A method for stimulating growth of human and animal cells cultured in vitro with a cell growth stimulatory amount of one or more gangliosides containing de-N-acetyl-sialic acid. A medicament and method for stimulating or inhibiting growth of human and animal cells by stimulating or inhibiting the production of growth stimulators selected from the group consisting of gangliosides containing de-N-acetyl-sialic acid, substances that promote synthesis of gangliosides containing de-N-acetyl-sialic acid and pharmaceutically acceptable salts thereof.

6 Claims, 15 Drawing Sheets

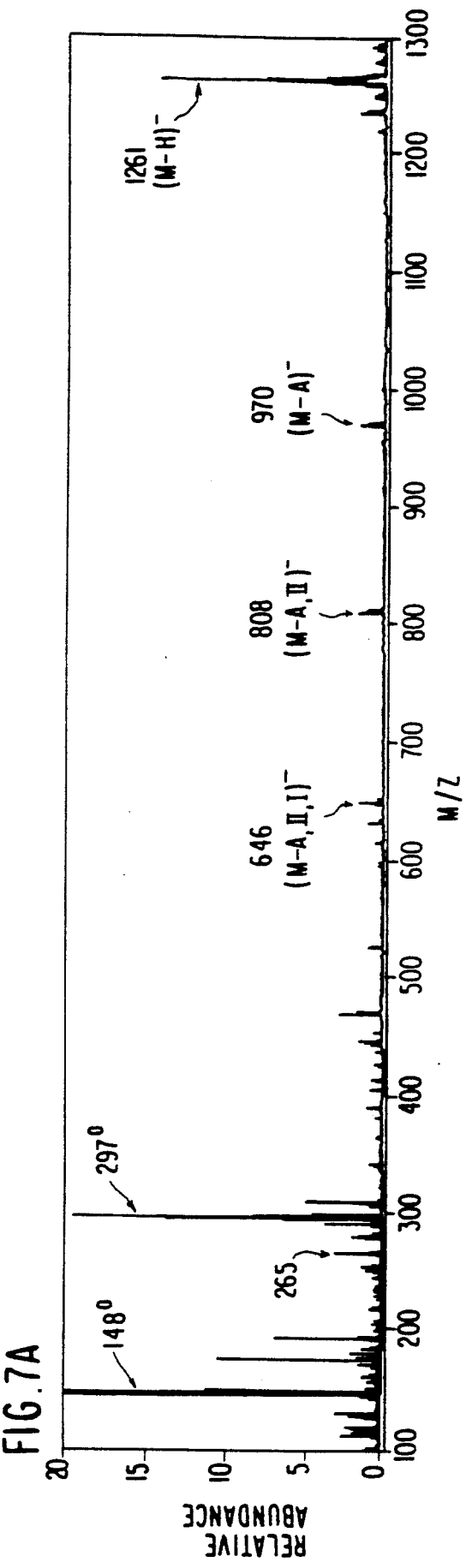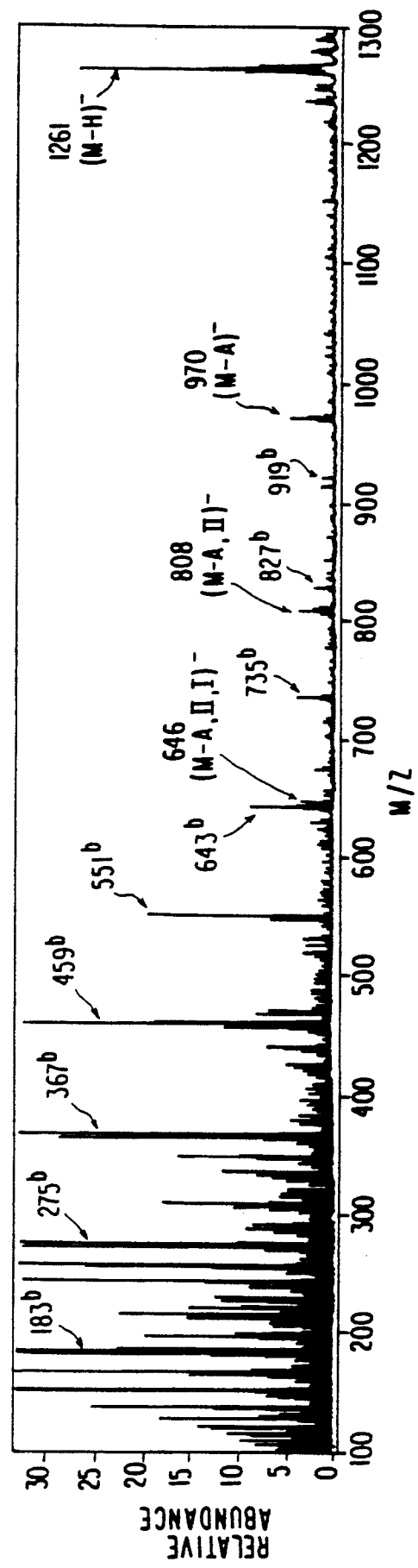

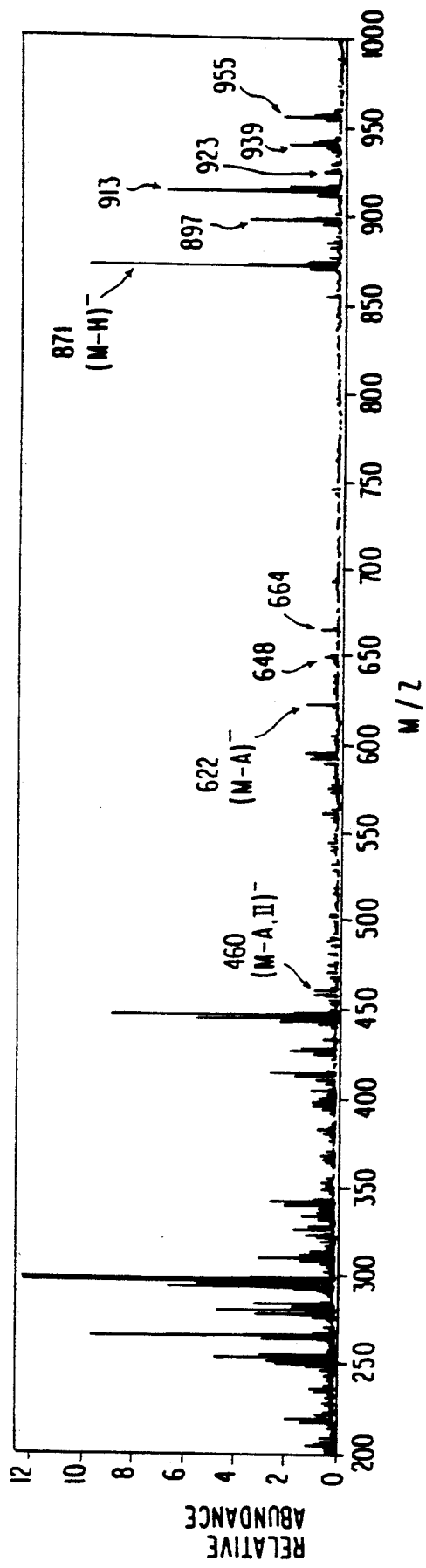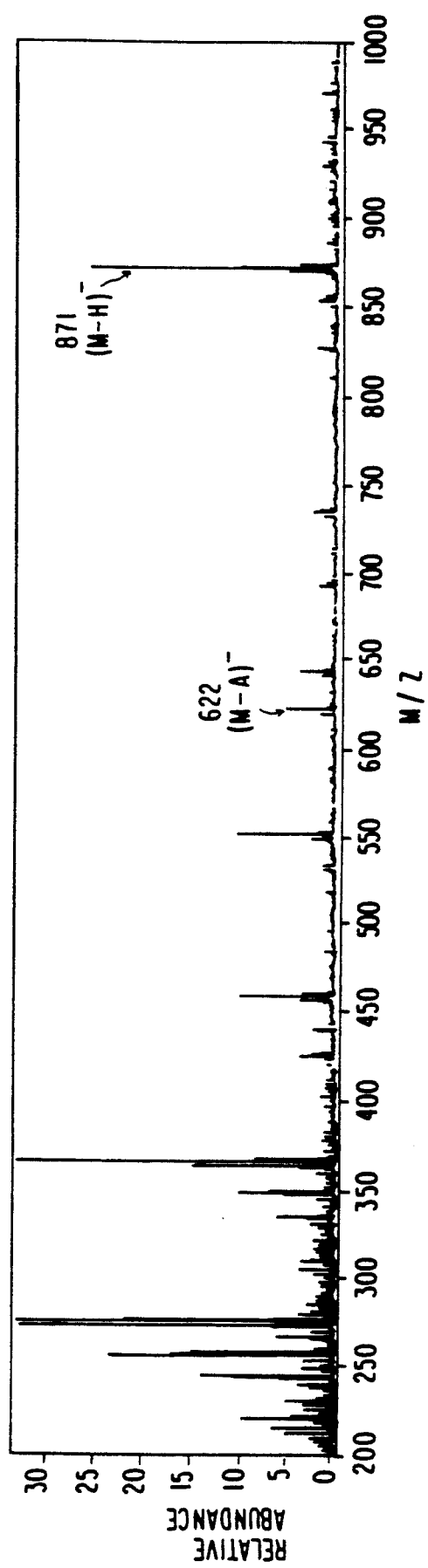

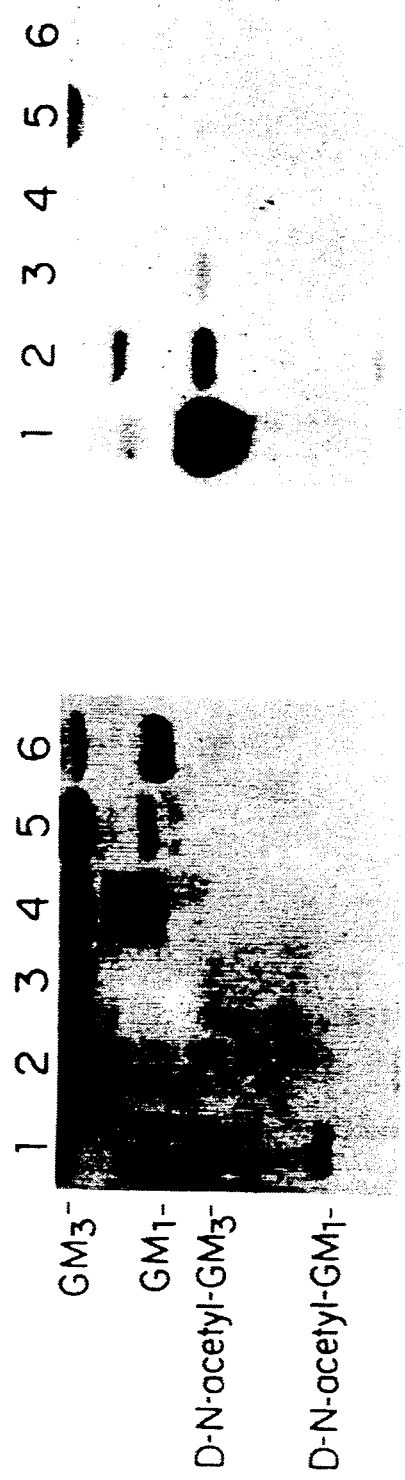

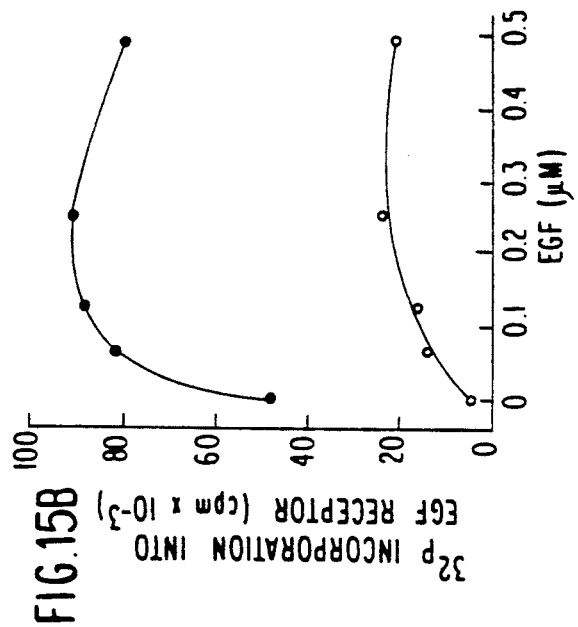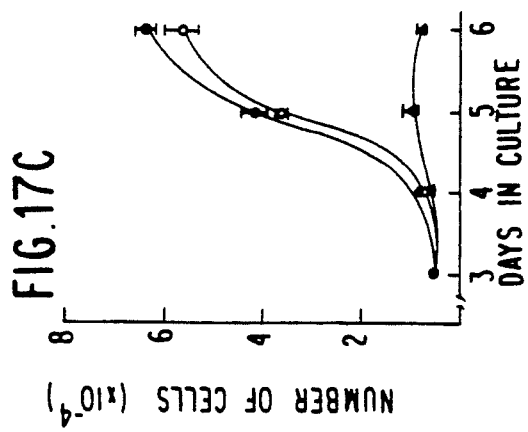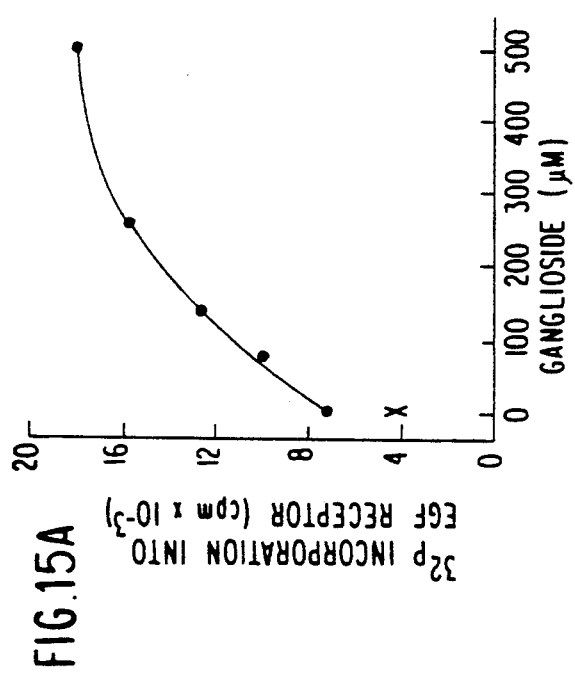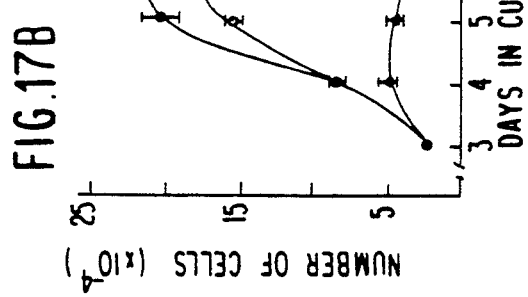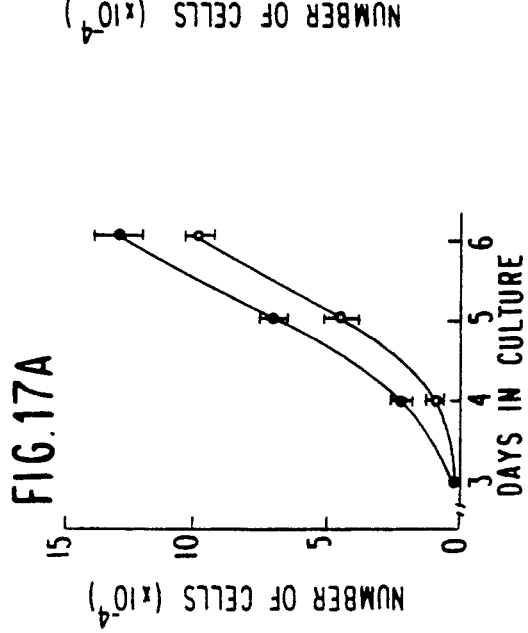

NATURALLY OCCURRING GANGLIOSIDES CONTAINING DE-N-ACETYL-SIALIC ACID AND THEIR APPLICATIONS AS MODIFIERS OF CELL PHYSIOLOGY

Portions of the invention(s) disclosed herein were supported in part by a grant from the National Cancer Institute, Department of Health and Human Services.

This application is a continuation-in-part application of copending applications U.S. Ser. No. 07/232.219 filed Aug. 15, 1988, now abandoned, U.S. Ser. No. 07/303,211 filed Jan. 30, 1989 (abandoned), of which are continuation-in-part applications of U.S. Ser. No. 07/155,401 filed Feb. 12, 1988 (abandoned).

FIELD OF THE INVENTION

The present invention relates to a method of preparing de-N-acyl glycosphingolipids from N-acylated glycosphingolipids and to methods of preparing lyso forms of glycosphingolipids from N-acylated glycosphingolipids and amino sugar-containing lyso form glycosphingolipids. The invention also relates to use of the above compounds to prepare labeled. e.g. radiolabeled, glycosphingolipids and lyso form glycosphingolipids.

This invention also relates to gangliosides containing de-N-acetyl-sialic acid (neuraminic acid) or N-trifluoroacetyl-sialic acid and their heretofore unknown effects on cell growth modification. More particularly, this invention relates to: (1) the natural occurrence of gangliosides containing de-N-acetyl sialic acid in various tumor cell lines and actively growing cells: (2) the effect of these gangliosides on cell growth both in vivo and in culture medium containing these gangliosides: (3) modification of the amino group of neuraminic acids in gangliosides which may further modify cell growth such as inhibiting tumor cell growth: (4) specific medicaments and methods for inhibiting or stimulating growth of human and animal cells, which medicaments and methods employ the above-mentioned gangliosides as well as substances that stimulate or block synthesis of the gangliosides: and (5) a substantially pure preparation of de-N-acetyl-gangliosides which have never before been identified.

BACKGROUND OF THE INVENTION

Glycosphingolipids are an important class of glycolipids and can be regarded as glycosides of N-acylsphingosine. These glycosphingolipids are generally divided into three classes: (1) neutral glycolipids. (2) sulfatides (sulfate-containing glycolipids), and (3) gangliosides (sialic acid- (N-acyl or O-acyl neuraminic acid) containing glycolipids).

Glycosphingolipids are also classified according to the number of sugar residues and according to the oligosaccharide core structures.

Besides gangliosides three series of neutral glycolipids are known, i.e., lacto, globo, and ganglio series. In addition, the simplest glycosphingolipids, containing only one carbohydrate, are known as cerebrosides. Currently, approximately 130 molecular species of glycosphingolipids are known, many of which are present at the cell surface membrane (Hakomori, S. (1986) *Scientific American* 254, 44–53).

Glycosphingolipids and, in particular, gangliosides are of great interest due to their activity as modifiers of cell physiology (E. Bremer, et al. (1986) *J. Biol. Chem.* 261, 2434-2440: S. Hakomori, et al., in G. Tettamanti, R. Ledeen, Y. Nagai, K. Sandhoff, and G. Toffano (Eds.), *Neuronal plasticity and gangliosides*, Liviana Press, Pavoda, 1986 pp. 201-214: and N. Hanai et al., (1987) *Biochem. Biochys. Res. Commun.*, 147, 127-134). Therefore, the synthesis of various glycosphingolipid derivatives and analogues is an important area of research.

Cell surface gangliosides may have two basic cellular functions: i) to mediate cell social functions (cell-cell, cell-microbe, or cell-matrix interactions), and ii) to modulate functional membrane proteins such as receptors and transporters (Hakomori, S (1981) *Ann. Rev. Biochem.* 50, 733-764). Ganglioside-mediated modulation of membrane receptor function has been suggested by the modification of protein kinase activity of epidermal growth factor (EGF) and platelet derived growth factor (PDGF) receptors by specific gangliosides ($GM_3$ or $GM_1$), but not by other types of glycolipids (Bremer, E., et al (1984) *J. Biol. Chem.* 259, 6818–6825 and Bremer, E., et al (1986) *J. Biol. Chem.* 261, 2434–2440).

For example, in A431 cells, which are characterized by a high content of EGF receptor, tyrosine phosphorylation of EGF receptors was specifically inhibited by exogenous addition of $GM_3$ but not by other gangliosides or neutral glycolipids (Bremer, E., et al (1986) *J. Biol. Chem.* 261, 2434–2440). Inhibition of the receptor kinase was demonstrated on the isolated EGF receptor after adsorption on an anti-receptor-antibody-Sepharose complex (Bremer, E., et al (1986) *J. Biol. Chem.* 261, 2434–2440). Further, exogenous addition of these gangliosides. $GM_3$ and $GM_1$, affects fibroblast growth factor- (FGF), EGF-, or PDGF-dependent cell growth stimulation in chemically-defined media (Bremer, E. et al (1986) *J. Biol. Chem.* 261, 2434–2440; Bremer, E., and Hakomori, S. (1982) *Biochem. Biophys. Res. Commun.* 106, 711–718: and Hakomori, S., et al (1986) in *Neuronal plasticity and gangliosides* (Tettamanti, G., Ledeen, R., Nagai, Y., Sandhoff, K., and Toffano, G., eds.), pp. 201–214. Liviana Press, Padova, Italy).

More recently, cytoskeletal protein kinase (Tsuji, S., et al (1983) *J. Biochem. (Tokyo)* 94, 303–306) has been found to be modified by gangliosides and various cell growth modulators such as retinoids, butyrate and 12-O-tetradecanoylphorbol-13-acetate (TPA) have been reported to induce changes in ganglioside synthesis when cell growth is arrested (Patt. L., et al (1978) *Nature* 273, 379–381; Fishman, P. H., et al (1974) *Biochem. Biochys. Res. Commun.* 59, 292–299; Huberman, E., et al (1979) *Cancer Res.* 39, 2618–2624; and Burczak, J. D. et al. (1983) *Exp. Cell Res.* 147, 281–286). On the other hand, sphingosines have been shown to have a nonspecific common inhibitory effect on protein kinase C activity (Hannun, Y. A., et al (1986) *J. Biol. Chem.* 261, 12604–12609).

Recently, various gangliosides ($GM_3$, $GM_2$, $GM_1$, and $GD_{1a}$) have been derivatized (S. Neuenhofer, G. et al (1985) *Biochemistry*, 24, 525–532) into their lyso forms, in which the amino groups of neuraminic acid and hexosamines were N-acetylated and only the amino group of the sphingosine was unsubstituted. For this derivatization, the amino group of the sphingosine was first blocked by a hydrophobic protective group (9-fluorenylmethoxycarbonyl), followed by acetylation of the amino groups of neuraminic acid and hexosamines, and subsequent removal of the protective group by liquid ammonia. The procedure involves several steps, and the yield is poor (about 30%).

The lyso form of $GM_3$ has been prepared (T. Taketomi and N. Kawamura, (1970) *J. Biochem. (Tokyo)* 68, 475-485) by treatment of $GM_3$ with a refluxing solution of 1M KOH in aqueous 90% butanol for 2.5 h. The product was claimed to have a strong hemolytic activity (twice that of lysolecithin) and was called lysosphingolipid or lysohematoside. The compound, however, had free amino groups at both neuraminic acid and sphingosine. (The term "neuraminic acid" is used according to the original definition (G. Blix, et al., (1957) *Nature* 179, 1088), i.e., de-N-acyl sialic acid is defined as "neuraminic acid", while N-acetyl, N-glycolyl and O-acyl derivatives of neuraminic acid are collectively called "sialic acid.")

Because of the remarkable cell growth modifying activities of gangliosides, potential application of gangliosides to modulation of in vitro and in vivo cell growth is an exciting area for investigation, Further, because gangliosides occur naturally in many cells, use of inhibitors or promoters of synthesis of particular gangliosides to abolish or enhance the natural effects of the gangliosides is also an exciting area for investigation. Unfortunately, because of the unpredictable cell growth modifying activities of different gangliosides which have been studied, e.g. $GM_3$ and $GM_1$, and because of lack of any coherent information as to what types of cells react to each ganglioside, little progress has been made in the area of in vitro or in vivo applications of gangliosides to modulate cell growth.

Accordingly, it would be desirable to be able to identify gangliosides that have the same effects on a variety of cells so that concrete in vitro or in vivo applications of the gangliosides can be identified and used for practical purposes.

SUMMARY OF THE INVENTION

Accordingly, one object of the present invention is to provide new methods of preparing de-N-acylated and N-acylated glycosphingolipids and lyso form glycosphingolipids which involve few steps and give a high yield.

Another object of the present invention is to provide novel methods of producing labeled glycosphingolipids.

These and other objects have been achieved by providing a method for preparing de-N-acylated forms of an N-acyl amino sugar and sialic acid containing glycosphingolipid comprising hydrolyzing the glycosphingolipids under mild alkaline conditions such that the N-acyl group of the amino sugar and sialic acid moiety is preferentially hydrolyzed.

The present invention also provides a method for preparing labeled N-acylated forms of amino sugar-containing glycosphingolipids comprising N-acylating the amino group on the sugar moiety with a labeled N-acylation reagent.

In another aspect, the present invention provides a method for preparing N-acylated forms of an amino sugar-containing lyso form glycosphingolipid comprising protecting the amino group of the sphingosine by incorporating the glycosphingolipid into a phospholipid, or hydrophobic matrix and then conducting selective N-acylation on the amino group of the sugar moiety.

Thus, the present invention also provides a method for preparing labeled N-acylated forms of amino sugar-containing glycosphingolipids comprising N-acylating the amino group on the sugar moiety with a labeled N-acylation reagent.

In an even further aspect, the present invention provides a method of preparing labeled N-acylated forms of an amino-sugar containing lyso form glycosphingolipid comprising protecting the amino group of the sphingosine by incorporating the glycosphingolipid into a phospholipid or hydrophobic matrix and then conducting selective N-acylation on the amino group of the sugar moiety with a labeled N-acylation reagent.

The present invention further provides a method for preparing labeled glycosphingolipids from an acylated sugar-containing lyso form glycosphingolipid comprising acylating the amino group on the sphingosine moiety with fatty acid containing labeled groups.

The above-described methods are especially applicable to gangliosides.

Another object of the present invention is to provide structural information about a new type of ganglioside that contains de-N-acetyl sialic acid which has not been previously known, obtained in purified form or synthetically synthesized.

Yet, another object of the present invention is to provide in vitro applications of these gangliosides to a wide range of cell types.

A further object of the present invention is to provide evidence that these gangliosides stimulate cell growth through promotion of phosphorylation of EGF, PDGF and/or FGF receptor or insulin receptor. Accordingly, inhibitors of synthesis of gangliosides containing N-modified sialic acid, such as gangliosides that contain N-trifluoroacetyl sialic acid, in general could be used as inhibitors of growth of specific types of cells such as tumor cells.

These and other objects of the invention have been accomplished by providing a substantially pure ganglioside containing de-N-acetyl-sialic acid.

The present invention also provides a culture medium for stimulating growth of human and animal cells comprising: (1) essential nutrients for cell growth, and (2) cell growth stimulatory amounts of one or more gangliosides containing de-N-acetyl-sialic acid.

In a particular embodiment, the culture medium is for stimulating insulin-dependent growth of human and animal cells comprising: (1) essential nutrients for cell growth, and (2) a cell growth stimulatory amount of one or more gangliosides containing de-N-acetyl-sialic acid.

The present invention further provides a method for stimulating growth of human and animal cells cultured in vitro comprising contacting the cells in culture with a cell growth stimulatory amount of one or more gangliosides containing de-N-acetyl-sialic acid.

In a particular embodiment, the method is for stimulating insulin-dependent growth of human and animal cells cultured in vitro comprising contacting the cells in culture with a cell growth stimulatory amount of one or more gangliosides containing de-N-acetyl-sialic acid.

In a further aspect, the present invention provides a medicament for stimulating growth of human and animal cells comprising: (1) a cell growth stimulatory amount of one or more growth stimulators selected from the group consisting of gangliosides containing de-N-acetyl-sialic acid, substances that promote synthesis of gangliosides containing de-N-acetyl sialic acid and pharmaceutically acceptable salts thereof; and (2) a pharmaceutically acceptable carrier, diluent or excipient.

The present invention also provides a method for stimulating growth of human and animal cells in vivo comprising contacting the cells with a cell growth stimulatory amount of gangliosides containing de-N-acetyl-sialic acid, substances that promote synthesis of gangliosides containing de-N-acetyl-sialic acid and pharmaceutically acceptable salts thereof.

In preferred embodiments, this medicament and method are used to promote wound healing.

In a particular embodiment, the present invention provides a medicament for stimulating insulin-dependent growth of human and animal cells comprising: (1) a cell growth stimulatory amount of one or more gangliosides containing de-N-acetyl-sialic acid, or pharmaceutically acceptable salts thereof: and (2) a pharmaceutically acceptable carrier, diluent or excipient.

In this particular embodiment the present invention also provides a method for stimulating insulin-dependent growth of human and animal cells in vivo comprising contacting said cells with a cell growth stimulatory amount of one or more gangliosides containing de-N-acetyl-sialic acid or pharmaceutically acceptable salts thereof, In an even further aspect, the present invention provides a medicament for inhibiting growth of human and animal cells comprising: (1) a cell growth inhibitory amount of one or more growth inhibitors that block synthesis of gangliosides containing de-N-acetyl-sialic acid and pharmaceutically acceptable salts thereof: and (2) a pharmaceutically acceptable carrier, diluent or excipient.

The present invention also provides a method for inhibiting growth of human and animal cells in vivo comprising contacting the cells with a cell growth inhibitory amount of one or more growth inhibitors that block synthesis of gangliosides containing de-N-acetyl-sialic acid and pharmaceutically acceptable salts thereof.

In preferred embodiments, this medicament and method are used to prevent or slow tumor growth and to prevent or slow metastasis of tumors.

Further, because N-trifluoroacetyl sialic acid or any other N-modified sialic acid could inhibit formation of de-N-acetyl-sialic acid, those gangliosides containing N-trifluoroacetyl sialic acid or any other N-modified sialic acid-containing gangliosides are expected to be strong inhibitors of cell growth, including tumor growth.

Also, in preferred embodiments for stimulating cell growth, the gangliosides containing de-N-acetyl-sialic acid comprise de-N-acetyl-$GM_3$ and de-N-acetyl-$GM_1$.

In embodiments relating to stimulating insulin-dependent cell growth, preferred gangliosides containing de-N-acetyl-sialic acid comprise sialyl 2→3 lactoneotetraosylceramide or sialyl 2→3 lactonorhexaosylceramide containing de-N-acetyl-sialic acid.

BRIEF DESCRIPTION OF THE DRAWINGS

FIG. 7 is a negative ion f.a.b.-mass spectra of dog erythrocyte $GM_3$ in A: triethanolamine (TEA) matrix, B:glycerol matrix. Ions are designated as in Table I: a: triethanolamine matrix cluster ions of formula (n[TEA]−1)$^-$, b: glycerol matrix cluster ions of formula (nG−1)$^-$, wherein G represents glycerol.

FIG. 9 is a negative ion f.a.b.-mass spectra of de-N-acetyl-lyso-$GM_3$ ($D_2$) in A: a triethanolamine matrix, B: a glycerol matrix.

FIG. 13 shows de-N-acetyl-GM$_3$ detection in the monosialoganglioside fraction of various cell lines and tissues by TLC immunostaining with monoclonal antibody DH5. Panel A: resorcinol/HCl staining: panel B: immunostaining. Lane 1, standard GM$_3$, GM$_1$, de-N-acetyl-GM$_3$, de-N-acetyl-GM$_1$ (GM$_1$ containing neuraminic acid): lane 2. B16 melanoma tumor grown in vivo lane 3, B16 cells cultured in vitro; lane 4, Swiss 3T3 cells cultured in vitro lane 5, rat liver; lane 6. rat brain.

FIG. 15 is two graphs showing the effect of de-N-acetyl-GM$_3$ on in vitro phosphorylation of EGF receptor depending on ganglioside concentration (A) and on EGF concentration (B). Concentration of Triton X-100 was 0.025%. Panel A: EGF concentration was 0.33 μM. Panel B: de-N-acetyl-GM$_3$ concentration was 500 μM. Closed circles, de-N-acetyl-GM$_3$; open circles, control without ganglioside addition: (X), no EGF.

FIG. 17 is graphs showing the effect of exogenously added de-N-acetyl-GM$_3$ and GM$_3$ on cell growth. A431 cells (panel A). Swiss 3T3 cells (panel B). and B16 cells (panel C). On the 3rd day of culture. 10 μM de-N-acetyl-GM$_3$ (closed circles) was added to A431 cells (panel A). Fifty μM de-N-acetyl-GM$_3$ (closed circles) was added to Swiss 3T3 cells (panel B). Fifty μM de-N-acetyl-GM$_3$ (closed circles) or 50 μM GM$_3$ (closed triangles) was added to B16 cells (panel C). For control (open circles) no ganglioside was added. Each data point shown is the average of 4 determinations ±S.E.

DETAILED DESCRIPTION OF THE INVENTION

This application is a continuation-in-part of copending applications U.S. Ser. No. 07/232,219 filed Aug. 15, 1988, and U.S. Ser. No. 07/303,211 filed Jan. 30, 1989, both of which are continuation-in-part applications of U.S. Ser. No. 07/155,401 filed Feb. 12, 1988 (abandoned). The entire disclosures of each of these three applications are incorporated herein by reference.

For the purposes of this invention, the following terms have the following meanings:

Glycosphingolipid—The term "glycosphingolipid" as used in this application indicates glycosphingolipids, which are the glycosides of N-acyl-sphingosine, the trivial name of which is ceramide. Sphingosines are a group of related long chain aliphatic 2-amino-1,3-dihydroxy-(long chain bases), of which D-erythro-1,3-dihydroxy-2-amino-2,5-transoctadecene occurs most frequently.

Lyso form glycosphingolipid—Lyso-sphingolipids as the term is used in this application are sphingolipids in which N-fatty acyl groups linked to amino group of sphingosine are eliminated. Lyso-GM$_3$ is therefore sialyl-lactosylsphingosine or sialyl-Galβ1→4Glcβ1→sphingosine; lyso-GM$_1$ is Galβ1→3GalNAc-β1→4[sialyl2→3]Galβ1→4Glcβ1→sphingosine, etc.

De-N-acylated glycosphingolipid or lyso form glycosphingolipid—De-N-acylated glycosphingolipids or lyso glycosphingolipids as used in this application are both de-N-fatty-acylated and de-N-acetylated or de-N-glycolylated compounds. N-acetyl and N-glycolyl are originally linked at the sialic acid and N-acetyl linked at the hexosamine of the sugar chain.

Amino sugar-containing glycosphingolipid or lyso form glycosphingolipid—Amino sugar-containing glycosphingolipids and lyso glycosphingolipids as used in this application are globo-series, lacto-series, and ganglio-series structures. Globo series contain N-acetyl-galactosamine at the terminus, ganglio series contain N-acetyl-galactosamine at the penultimate position, while lacto-series contain N-acetyl-glucosamine at the penultimate position. These are the simplest forms. Chains are further extended to create a large diversity of structures.

Ganglioside—Glycosphingolipids containing sialic acid (nonulosaminic acid or neuraminic acid containing an N-acetyl, N-glycolyl or O-acetyl group). The nomenclature used to designate ganglio-series gangliosides (e.g., GM$_1$, GM$_2$, GM$_3$, etc.) is according to Svennerholm. L., J. Neurochem., 10 (1963) 613–623.

Lyso form ganglioside—Glycosphingolipids in which N-fatty acyl groups linked to the amino group of sphingosine are eliminated.

Ganglioside containing de-N-acetyl-sialic acid—A ganglioside, as defined above, that contains neuraminic acid. The term "neuraminic acid" is used as originally defined by Blix. Gottschalk, and Klenk, (1957) Nature 179, 1088. i.e. nonulosaminic acid without N- or O-substitution.

Figure 1:
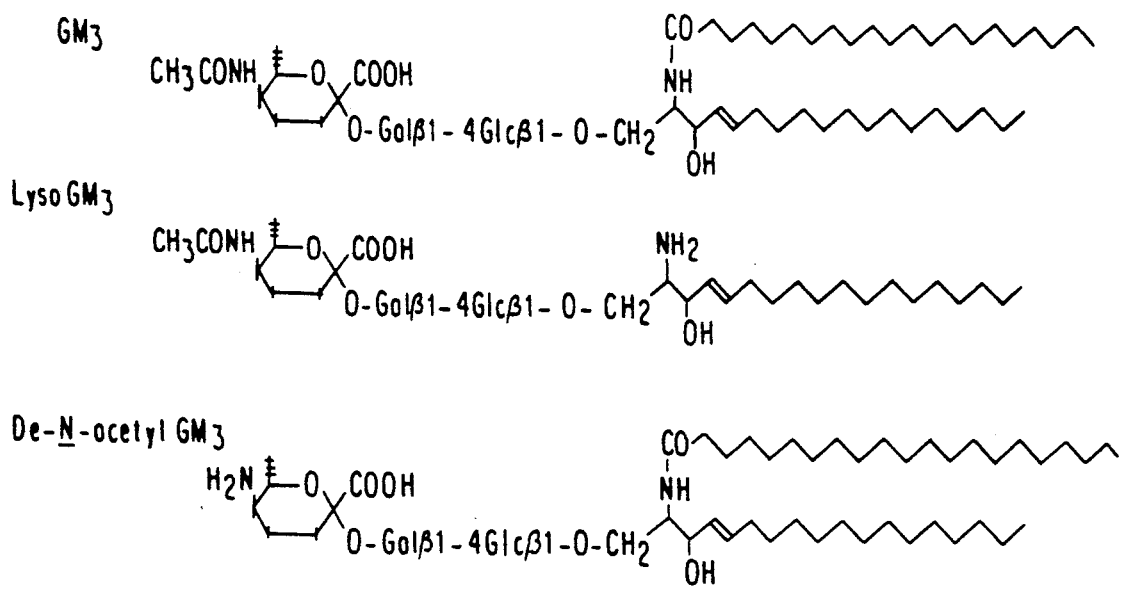
FIG. 1 shows the structures of $GM_3$, lyso-$GM_3$, and de-N-acetyl-$GM_3$. The glycolipids are abbreviated according to the system of Svennerholm (Svennerholm, L., (1963) *J. Neurochem.* 10, 613-623) for ganglio-series gangliosides.

GM$_3$—A ganglioside having the structure shown in FIG. 1.

Lyso GM$_3$—A ganglioside having the structure in FIG. 1.

De-N-acetyl-GM$_3$—A GM$_3$ ganglioside containing neuraminic acid. i.e. de-N-acetyl sialic acid having the structure shown in FIG. 1.

De-N-acetyl-GM$_1$—A GM$_1$ ganglioside containing neuraminic acid.

Sialyl 2→3 lactonorhexaosylceramide—A ganglioside having the structure: VI³NeuAcnLc$_6$.

Sialyl 2→3 lactoneotetraosylceramide—A ganglioside having the structure: IV³NeuAcnLc$_4$.

SYNTHESIS OF GLYCOSPHINGOLIPIDS

The novel methods of synthesizing the glycosphingolipids according to the present invention will now be described in detail.

Isolation or preparation of glycosphingolipid starting material

The synthesis of the de-N-acylated glycosphingolipid and the acylated lyso form glycosphingolipid according to the present invention can be accomplished by using the corresponding N-acylated glycosphingolipid as the starting material.

General method for purification of N-acylated glycosphingolipids (in which the amino group of sphingosine is N-fatty acylated having C14–C24 aliphatic chains and the amino group of hexosamine in the sugar chain is N-acetylated and the amino group of neuraminic acid in the sugar chain is N-acetylated or N-glycolylated): The starting material as defined above, i.e., various types of gangliosides or amino sugar-containing glycosphingolipids, is prepared from natural sources after extraction with isopropanol-hexane-water, chloroform-methanol, or 90% ethanol, followed by various steps of purification. including Folch's partition, ion exchange chromatography in chloroform-methanol-water, high pressure high performance liquid chromatography, etc., as described in Hakomori, S. (1983) In: *Handbook of Lipid Research Vol. 3, Sphingolipid Biochemistry* (Kanfer, J. N., Hakomori, S., eds.), Plenum Publishing. New York, pp. 1–165. Glycosphingolipids can be synthesized by pure organic synthesis; however, the yield of such synthesis is extremely poor and involves a great many steps (see Hakomori, Id. above). Therefore, the starting material for preparation of the various derivatives preferably is not a synthetic compound.

When the desired modified glycosphingolipid is a ganglioside, the synthesis of the de-N-acyl ganglioside and lyso form ganglioside can be accomplished by using the corresponding unmodified ganglioside containing N-acetyl and/or N-glycolyl neuraminic acid as the starting material.

The unmodified ganglioside containing N-acetyl and/or N-glycolyl neuraminic acid to be used as the precursor for the ganglioside containing de-N-acyl-sialic acid is obtained by extraction from an appropriate source readily known to the skilled artisan (e.g. dog erythrocytes for $GM_3$ and bovine brain for most other gangliosides) and purified by chromatography (R. K. Yu and R. W. Ledeen (1972) *J. Lipid Res.* 13, 680–686) on DEAE Sephadex followed by high-performance liquid chromatography on a column of Iatrobeads 6RS8010 using various gradient elution systems well known in the art (for example, see K. Watanabe and Y. Arao (1981) *J. Lipid Res.* 22, 1020–1024).

Preparation of de-N-acyl glycosphingolipid

The N-acyl sugar-containing glycosphingolipid prepared or isolated as described above is subjected to a critical step of hydrolysis such that the N-acyl group on the sugar moiety is preferentially hydrolyzed.

Specifically, the N-acyl group of the sugar moiety of the N-acyl sugar-containing glycosphingolipid is preferentially hydrolyzed by treatment under mild alkaline conditions.

The mild alkaline conditions comprise using a base at a concentration of about 0.1M or below, and preferably the concentration of the base is about 0.1M.

A suitable base that can be used is an alkali metal hydroxide and preferably the base is sodium hydroxide.

The reaction is conducted in a suitable solvent such as 90% 1-butanol at a temperature of about 80° C. for about 4 hours.

The yield is generally greater than 70%.

After completion of the reaction, the hydrolysate in the solvent is neutralized with acid (e.g., 12M HCl) and taken to dryness. The residue is resuspended in water in any convenient volume and purified by an appropriate method such as by passing through a column of $C_{18}$ silica. The column is washed with water to eliminate salts and then the lipids, mostly glycosphingolipids that have been de-N-acylated, are eluted with an appropriate solvent (e.g., methanol). The derivative can be purified by high-performance liquid chromatography.

Preparation of lyso form glycosphingolipid

In order to prepare the lyso form glycosphingolipid, the N-acyl sugar-containing glycosphingolipid prepared or isolated as described above is deacylated and the fatty acid residue substituent on the amino group of the sphingosine moiety removed to prepare an intermediate compound, specifically a de-N-acylated lyso glycosphingolipid. One method by which this can be accomplished is by dissolving the glycolipid (about 6 μmol) in 1M KOH in aqueous 90% n-butanol and heating at about 117° C. for about 2 hours.

Under these conditions, greater than 95% of the glycolipid is converted to the de-N-acyl lyso form (Taketomi, T. and Yamakawa, (1963) T., *J. Biochem.* (Tokyo), 54, 444–451).

Next, the sugar moiety of the de-N-acyl lyso glycosphingolipid is preferentially N-acylated by protecting the free amino group of the sphingosine moiety.

Protection of the amino group of sphingosine of de-N-acetyl lyso form glycosphingolipids can be by PC-liposome or by any other type of phospholipid or hydrophobic matrix that interacts with the sphingosine moiety of the lyso form glycosphingolipid. Dimyristoyl- or distearyl-PC, sphingomyelin, diacetylphosphate, and any other synthetic compounds that offer hydrophobic interaction with sphingosine hydrocarbons of lyso form glycosphingolipid analogs are satisfactory. This can be extended to solid-phase interaction of lyso form glycosphingolipid analogs with a long chain alkylated silica gel matrix, which interacts with lyso form glycosphingolipid analogs. In that case, the amino group of amino sugar or neuraminic acid can be N-acylated selectively. Lyso form glycosphingolipid analogs, as mentioned above, include glycosylated sphingosine containing de-N-acetylated or de-N-glycolylated neuraminic acid or de-N-acetylated hexosamines (glucosamine or galactosamine).

Especially useful matrices are dp-PC liposomes.

In order to incorporate the de-N-acyl-lyso-glycosphingolipid into a matrix the de-N-acyl-lyso-glycosphingolipid is mixed together with the phospholipid or hydrophobic substance in a molar ratio of about 1 to 10 in a suitable solvent and the mixture dried.

The de-N-acyl-lyso-glycosphingolipid/liposome complex is then resuspended by sonication, or other appropriate method, in a solution of DEC (dimethylaminopropylethylcarbodiimide) in water (about 20 mg DEC/1 ml $H_2O$). The suspension is cooled to about 4° C. and the N-acylation reaction is initiated by adding an appropriate buffer (e.g., for N-acetylation. 0.1M acetate buffer (about 0.2 ml, pH about 5.2/ml suspension)). The suspension is incubated for about 24 hours at about 4° C. and the reaction stopped by the addition of ethanolamine (to about 20 μmol) followed by chloroform-methanol (2:1 by volume) (about 5 ml chloroform-methanol/1.2 ml suspension). Two phases are formed and the lower phase is washed with the same volume of chloroform-methanol-water (3:47:48 by volume). Two phases are again formed and the upper phases from each wash are combined, dried, resuspended in water, desalted (e.g., by passage through a $C_{18}$ silica column) and purified by high-performance liquid chromatography to give the lyso glycosphingolipid in 70–80% yield.

Preparation of labelled glycosphingolipids

As mentioned above, the present invention also provides novel methods for producing labeled glycosphingolipids.

Preparation of labeled acylated forms of amino sugar-containing glycosphingolipids labeled in the sugar moiety According to the present invention a method is provided for producing an N-acylated glycosphingolipid wherein the acyl group of the sugar moiety is labeled.

N-acylation reagents in general include N-acyl anhydride or N-acyl chloride or a mixture of protonated acyl group with carbodiimide catalysts. The acyl group can be labeled with $^{14}C$ and/or $^{3}H$. The N-acylation reaction proceeds much more easily than an O-acylation reaction, and the yield is nearly 100%.

As one example, in order to prepare a radiolabeled N-acetylated glycosphingolipid, an amino sugar-containing glycosphingolipid which can be obtained, for example, by the method described above for preparing de-N-acylated glycolipids, can be N-acetylated by dissolving the amino sugar-containing glycolipid in an appropriate solvent containing DEC (dimethylaminopropylethylcarbodiimide) (2 mg/ml H$_2$O for example), cooling to about 4° C. and adding acetate buffer prepared from radiolabeled (e.g. $^{14}C$ or $^{3}H$) acetic acid to a final concentration of about 0.02M acetate. The mixture is incubated for about 24 hours at 4° C. and the reaction stopped by addition of ethanolamine (to about 20 $\mu$mol). The radiolabeled compound is purified by high-performance liquid chromatography or other suitable method to give the radiolabeled glycolipid.

Alternatively, as another example, the de-N-acyl glycolipid can be N-acetylated with [$^{14}C$] or [$^{3}H$]-acetic anhydride as follows.

Dried samples of the de-N-acetyl glycolipid are dissolved in NaHCO$_3$ (about 0.5M) by stirring and heating at about 60° C. $^{14}C$-acetic anhydride in methanol is added in a volume to bring the NaHCO$_3$ concentration to about 0.1M and the mixture is incubated for about 1 hour at about room temperature. After drying under a nitrogen stream, the reaction mixture is dissolved in distilled water and purified by an appropriate method such as by use of a C$_{18}$ silica gel column. Labeled glycolipid can be eluted with chloroform:methanol and analyzed by HPTLC through HPLC by Iatrobeads 6RS8010.

Preparation of labeled acylated glycosphingolipids labeled in the fatty acid moiety According to this method of the present invention, a fatty acylated glycosphingolipid labeled in the fatty acid moiety can be prepared from an N-acylated lyso form glycosphingolipid.

The N-acylated lyso form glycosphingolipid can be prepared as described above.

The N-acylated lyso form glycosphingolipid, after purification from the liposome or other matrix is dissolved in an appropriate solvent containing DEC and fatty acid is added which contains a labeled group. Alternatively an acyl chloride of fatty acids can be used as an acylating reagent of the amino group of sphingosine. Suitable fatty acid residues for linking to the amino group of sphingosine include C14–C24 in normal composition. Mostly, C16–C18 for one group, and C20–C24 for another group. Further, depending on the requirement, an $\alpha$-hydroxylated fatty acid or any other substituted fatty acid, including radiolabeled, spin-labeled, or fluorescent-labeled group can be used. The skilled artisan can readily determine how to use these labeled fatty acids. The radiolabel can be, for example, $^{14}C$ or $^{3}H$.

After incubating at an appropriate temperature for an appropriate amount of time, the thus formed fatty acid labeled glycosphingolipid is separated from the reaction mixture and purified by high-performance liquid chromatography, or other suitable method to give the fatty acid labeled glycosphingolipid.

An N-acetylated glycosphingolipid labeled in both the N-acetyl group of the sugar moiety and the fatty acid moiety can be produced according to the same methods except that the starting material is an N-acylated lyso form labeled in the N-acyl group on the sugar moiety produced according to the method described below.

Preparation of labeled N-acetylated lyso form glycosphingolipids labeled in the N-acyl group on the sugar moiety The method for preparing N-acylated lyso form glycosphingolipids labeled in the N-acyl group on the sugar moiety is analogous to the above-described method for preparing the lyso form glycosphingolipids except that the N-acylation reaction is a reaction initiated by adding acetate buffer (about 0.1M) containing labeled (e.g. $^{14}C$ or $^{3}H$) acetic acid or other suitable N-acylation reagents.

NOVEL NATURALLY OCCURRING GANGLIOSIDES CONTAINING DE-N-ACETYL-SIALIC ACID AND THEIR APPLICATIONS AS MODIFIERS OF CELL PHYSIOLOGY

Of the gangliosides containing de-N-acetyl-sialic acid useful in the present invention, one, de-N-acetyl-GM$_3$ has been shown by the present inventors to exist in nature as a component of cells. This is the first time that any ganglioside containing de-N-acetyl-sialic acid has been identified, either as naturally existing or as a synthetic compound, and shown to display biological activities.

These gangliosides were found in various tumor cell lines and human tumor tissue but have not been detected in normal cell lines and normal human tissue.

According to the present invention it has been unexpectedly found that gangliosides containing de-N-acetyl-sialic acid possess a strong stimulatory effect on growth of numerous human and animal cell lines when added to culture media. These modified gangliosides also promote growth factor receptor associated kinase activities. Additionally, some gangliosides containing de-N-acetyl-sialic acid promote insulin dependent cell growth.

However, the particular growth factor receptor associated kinase affected appears to differ depending upon the particular ganglioside that is modified, e.g. GM$_3$, GM$_1$, sialyl 2→3 lactonorhexaosylceramide or sialyl 2→3 lactoneotetraosylceramide.

For example, de-N-acetyl-GM$_3$ gangliosides appear to exert their effects by acting on EGF and PDGF receptor kinase, whereas de-N-acetyl-GM$_1$ gangliosides appear to exert their effects by acting on PDGF receptor kinase. In contrast, de-N-acetyl 2→3 lactonorhexaosylceramide and de-N-acetyl 2→3 lactoneotetraosylceramide are expected to exert their effects by acting on insulin receptor kinase. However, the precise manner in which the modified gangliosides actually act, e.g. on various kinases, is not firmly established and, accordingly, the inventors do not want to be bound by the above explanation.

Culture Medium and Method for Stimulating Growth of Cells in vitro

As a result of the discovery by the present inventors of the growth stimulatory effects of gangliosides containing de-N-acetyl-sialic acid, the present invention provides a culture medium for stimulating growth of human and animal cells comprising: (1) essential nutrients for cell growth, and (2) a cell growth stimulatory amount of one or more gangliosides containing de-N-acetyl-sialic acid.

The present invention also provides a method for stimulating growth of human and animal cells cultured in vitro comprising contacting said cells in culture with a cell growth stimulatory amount of one or more gangliosides containing de-N-acetyl-sialic acid.

Examples of suitable gangliosides containing de-N-acetyl-sialic acid which can be used in the culture medium and method include de-N-acetyl-$GM_3$, de-N-acetyl-$GM_1$, de-N-acetyl $GM_2$, and $GD_{1a}$, $GD_{1b}$, $GT_{1b}$, containing de-N-acetyl-sialic acid, etc.

De-N-acetyl-$GM_3$ and de-N-acetyl-$GM_1$ are preferred and de-N-acetyl-$GM_3$ is especially preferred.

For insulin-dependent cell growth, sialyl 2→3 lactoneotetraosylceramide and sialyl 2→3 lactonorhexaosylceramide containing de-N-acetyl-sialic acid are preferred, and sialyl 2→3 lactoneotetraosylceramide containing de-N-acetyl-sialic acid is especially preferred.

The de-N-acetyl-gangliosides can be synthesized as described below in detail in a separate section.

As the culture media that can be used in the present invention, any culture medium conventionally used to culture the particular human or animal cells of interest can be used. Such a culture medium would, at a minimum include essential nutrients for cell growth, i.e., glucose, amino acids, glutamine, vitamins, insulin, transferrin, hydrocortisone, trace metal elements, and, depending on the cells. EGF, PDGF, and/or FGF.

Enriched media can also be used.

Further, the media can be liquid or semi-solid, (e.g. including soft agar or methylcellulose gel).

Examples of suitable culture media include Eagle's Basic Medium, Dulbecco's Modified Eagle's Medium, Ham's Medium, Sato's Chemically Defined Medium, etc.

The gangliosides containing de-N-acetyl-sialic acid are added to the cell culture medium as follows.

Purified ganglioside containing de-N-acetyl-sialic acid is dissolved in a suitable organic solvent (e.g. chloroform:methanol (2:1 v/v) and evaporated under an inert atmosphere (e.g. a nitrogen stream). The residue is then dissolved in the culture medium at the desired concentration, sonicated, and passed through a sterilizing filter (e.g. 0.2 μ pore diameter).

The media can be prepared fresh for use or can be prepared and then stored for as long as one month or more at 4° C.

The gangliosides containing de-N-acetyl-sialic acid are added to the final culture media in a concentration sufficient to promote cell growth, Whether a particular cell line is susceptible to the growth promoting effect of the gangliosides containing de-N-acetyl-sialic acid and at what concentrations susceptibility is exhibited can readily be determined by the skilled artisan by culturing cells in a series of concentrations of the gangliosides containing de-N-acetyl-sialic acid and then determining the growth of the cells over time at each concentration point as compared to a standard where no modified ganglioside is added.

In the case of tumor cells, which synthesize gangliosides containing de-N-acetyl-sialic acid, the growth promoting effects are small. However, normal cells which do not appear to synthesize gangliosides containing de-N-acetyl-sialic acid react strongly to exogenous addition of gangliosides containing de-N-acetyl-sialic acid.

Suitable concentrations of gangliosides containing de-N-acetyl-sialic acid that stimulate cell growth generally range from about 10 to about 30 μg/ml.

The above-described culture media and method for stimulating cell growth of human and animal cells are especially applicable to mammalian cells such as, for example, 3T3 cells, WI38 cells, BKH cells, etc.

Cell lines that appear less susceptible to the growth promoting effects of the exogenously added de-N-acetyl-$GM_3$ or de-N-acetyl-$GM_1$ are those cells which are capable of producing those gangliosides endogenously, such as B16 myeloma cells.

By use of the above described culture media and method, human and animal cell growth in vitro can be increased by as much as 50-100% or more.

Medicament and Method for Stimulating or Inhibiting Cell Growth in vivo

The inventors have detected the natural occurrence of gangliosides containing de-N-acetyl-sialic acid in human and animal cells, and thus not only can these gangliosides be used to stimulate cell growth, but additionally, substances that promote or block the cellular synthesis of these modified gangliosides can also be used in the present invention to inhibit or stimulate, respectively, growth of human and animal cells that synthesize these modified gangliosides.

The natural occurrence of the modified gangliosides in various cells can be detected by the following method.

Cells are cultured according to methods appropriate for the cells, harvested, and pelleted by centrifugation. The pellets are extracted with a suitable solvent (e.g. chloroform:methanol (2:1, v/v/)), followed by three partitions with water according to known methods, such as the modified method of Folch (Folch-Pi, J., et al (1951) *J. Biol. Chem.* 191, 819-831). The Folch upper phases are then combined, evaporated to a convenient volume, and salt is removed by suitable means, such as by passing the sample through a $C_{18}$ silica gel column (Kundu, S. K. and Sukuzi, A. (1985) *J. Chromatogr.* 224, 249-256). followed by DEAE-Sephadex Chromatography (Ledeen, R. W. and Yu, R. K. (1982) *Meth. Enzymol.* 83, 139-191 and Nores, G. and Caputto, R. (1984) *J. Neurochem.* 42, 1205-1211). The monosialoganglioside fraction is then eluted with a suitable solvent (e.g. chloroform:methanol:0.08M ammonium formate (30:60:8, v/v/v), desalted again (e.g. with a $C_{18}$ silica gel column) and evaporated to dryness (e.g. in a rotary evaporator).

The dried material is then subjected to a method for fractionating the particular gangliosides.

For example, the dried material can be applied to a porous silica gel column of Iatrobeads 6RS8010 (a porous silica gel manufactured by Iatron Chemical Co., Kanda, Tokyo, Japan) which is equilibrated with n-propanol-15% aqueous ammonium hydroxide (75:15, v/v). and eluted with a gradient from the same solvent to n-propanol-15% aqueous ammonium hydroxide (75:25 v/v) over an amount of time sufficient to elute the desired gangliosides in separate fractions (e.g. over 200 minutes using Varian 500 HPLC equipment). The eluates are collected in fractions suitable to keep the desired gangliosides separate (e.g. 2 ml/fraction when eluting over 200 minutes using Varian 500 HPLC equipment), and each fraction is analyzed by HPTLC.

By the above method, unmodified gangliosides and gangliosides containing de-N-acetyl-sialic acid can be eluted separately in that order and with no overlap.

The particular gangliosides eluted can be identified by methods described below (e.g. NMR spectroscopy and negative ion f.a.b.).

According to this method, it is possible to determine whether particular cells carry gangliosides containing de-N-acetyl-sialic acid and thus whether treatment with stimulators and/or inhibitors of synthesis of these modified gangliosides would be appropriate.

As a result of the discovery by the present inventors of the growth stimulatory effects of gangliosides containing de-N-acetyl-sialic acid and the presence of de-N-acetyl-gangliosides in various cells, the present invention provides a medicament for stimulating growth of human and animal cells comprising:

(1) a cell growth stimulatory amount of one or more growth stimulators selected from the group consisting of gangliosides containing de-N-acetyl-sialic acid, substances that promote synthesis of gangliosides containing de-N-acetyl-sialic acid and pharmaceutically acceptable salts thereof, and (2) a pharmaceutically acceptable carrier, diluent or excipient.

Similarly, the present invention also provides a method for stimulating growth of human and animal cells in vivo comprising contacting said cells with a cell growth stimulatory amount of gangliosides containing de-N-acetyl-sialic acid, substances that promote synthesis of gangliosides containing de-N-acetyl-sialic acid, and pharmaceutically acceptable salts thereof.

As the ganglioside containing de-N-acetyl-sialic acid or its pharmaceutically acceptable salts, any ganglioside containing de-N-acetyl-sialic acid as defined above or its pharmaceutically acceptable salt can be used.

Examples of suitable gangliosides containing de-N-acetyl-sialic acid which can be used in the medicament and method for stimulating cell growth in vivo include those described above for use in the culture medium of the present invention and their pharmaceutically acceptable salts.

De-N-acetyl-$GM_3$ and de-N-acetyl-$GM_1$ are preferred and de-N-acetyl-$GM_3$ is especially preferred.

Suitable substances and their pharmaceutically acceptable salts that promote synthesis of gangliosides containing de-N-acetyl-sialic acid can be determined by the skilled artisan and include, for example, N-acetylase.

N-acetylase can be obtained by methods readily determined by the skilled artisan.

The above-described medicament and method for stimulating in vivo growth of human and animal cells are especially applicable to treatment of mammalian cells and especially to cells that are involved in wound healing.

In a more particular embodiment, the present invention provides a medicament for stimulating insulin-dependent growth of human and animal cells comprising: (1) a cell growth stimulatory amount of one or more gangliosides containing de-N-acetyl-sialic acid, or pharmaceutically acceptable salts thereof: and (2) a pharmaceutically acceptable carrier, diluent or excipient.

The present invention, in this more particular embodiment also provides a method for stimulating insulin-dependent growth of human and animal cells in vivo comprising contacting said cells with a cell growth stimulatory amount of one or more gangliosides containing de-N-acetyl-sialic acid or pharmaceutically acceptable salts thereof.

Examples of suitable gangliosides containing de-N-acetyl-sialic acid or their pharmaceutically acceptable salts include those defined above for use in the culture medium for stimulating cell growth and their pharmaceutically acceptable salts.

Sialyl 2→3 lactoneotetraosylceramide and sialyl 2→3 lactonorhexaosylceramide containing de-N-acetyl-sialic acid are preferred, and sialyl 2→3 lactoneotetraosylceramide containing de-N-acetyl-sialic acid is especially preferred.

Also as a result of the discovery by the present inventors of the growth stimulatory effect of gangliosides containing de-N-acetyl-sialic acid in various cells, the present invention provides a medicament for inhibiting growth of human and animal cells comprising:

(1) a cell growth inhibitory amount of one or more growth inhibitors that block synthesis of gangliosides containing de-N-acetyl-sialic acid and pharmaceutically acceptable salts thereof; and (2) a pharmaceutically acceptable carrier, diluent or excipient.

Similarly, the present invention also provides a method for inhibiting growth of human and animal cells in vivo comprising contacting said cells with a cell growth inhibitory amount of one or more growth inhibitors that block synthesis of de-N-acetyl-gangliosides or pharmaceutically acceptable salts thereof.

Suitable substances and their pharmaceutically acceptable salts that block synthesis of gangliosides containing de-N-acetyl-sialic acid can be determined by the skilled artisan, and include, for example, anti-N-deacetylase. Various N-modified gangliosides and lyso form gangliosides such as gangliosides and lyso form gangliosides containing N-trifluoroacetyl sialic acid, N-carbamyl acetyl sialic acid, N-propyl sialic acid, N-dichloroacetyl sialic acid and N-trichloroacetyl sialic acid are also considered appropriate inhibitors of synthesis of de-N-acetyl gangliosides.

Anti-N-deacetylase can be obtained by methods readily determined by the skilled artisan as can the various N-modified gangliosides and N-modified lyso form gangliosides (Hakomori, S. et al. (1980) "Cell Biological and Immunological Significance of Ganglioside Changes Associated with Transformation" in *Structure and Function of Gangliosides*, (Svennerholm, L. Dreyfus, H., Urban, P. S.—eds) Plenum Publishing Corp., N.Y. pp 247–261).

The above described medicament and method for inhibiting growth of human and animal cells are especially applicable to treatment of mammalian cells and especially to malignant or non-malignant tumor cells to prevent or slow tumor growth and to prevent or slow metastasis of tumors.

Suitable pharmaceutically acceptable carriers, diluents or excipients for the medicaments of the present invention depend upon the particular medical use of the medicament and can readily be determined by the skilled artisan.

Suitable methods of administration of the medicaments of the present invention depend upon the particular medical application and can readily be determined by the skilled artisan.

Suitable doses of the medicaments of the present invention depend upon the particular medical application, as well as the weight and sex of the subject, etc., and can readily be determined by the skilled artisan from in vitro data.

Synthesis of novel gangliosides containing de-N-acetyl-sialic acid

The synthesis of the novel gangliosides containing de-N-acetyl-sialic acid of the present invention will now be described.

The synthesis of the modified ganglioside can be accomplished by using the corresponding unmodified ganglioside containing N-acetyl neuraminic acid as the starting material.

The unmodified ganglioside containing N-acetyl neuraminic acid to be used as the precursor for the ganglioside containing de-N-acetyl-sialic acid is obtained by extraction from an appropriate source readily known to the skilled artisan (e.g. dog erythrocytes for $GM_3$ and bovine brain for most other gangliosides) and purified by chromatography (R. K. Yu and R. W. Ledeen (1972) *J. Lipid Res.* 13, 680–686) on DEAE Sephadex followed by high-performance liquid chromatography on a column of Iatrobeads 6RS8010 using various gradient elution systems well known in the art (for example, see K. Watanabe and Y. Arao (1981) *J. Lipid Res.* 22, 1020–1024).

The thus isolated unmodified ganglioside containing N-acetyl neuraminic acid is then used to prepare the ganglioside containing de-N-acetyl-sialic acid. A critical step in the preparation of the ganglioside containing de-N-acetyl-sialic acid is the use of mild alkaline conditions of hydrolysis under which the N-acetyl group of sialic acid is preferentially hydrolyzed.

Specifically, the N-acetyl group of the sialic acid portion of the unmodified ganglioside is preferentially hydrolyzed to give the de-N-acetyl form on treatment with 0.1M NaOH in aqueous 90% 1-butanol at about 80° for about 4 hours. The yield is generally greater than 70%. The hydrolysate in aqueous 1-butanol is then neutralized with acid. e.g. 12M HCl, and taken to dryness. The residue is resuspended in water in any convenient volume and passed through a column of $C_{18}$ silica. The column is washed with water to eliminate salts and then the lipids, mostly gangliosides containing de-N-acetyl-sialic acid, are eluted with an appropriate solvent (e.g., methanol). The derivative is purified by high-performance liquid chromatography.

The synthesis of the ganglioside containing de-N-acetyl-sialic acid is described in detail in Example 1 by reference to $GM_3$. However, the procedures described for $GM_3$ can be applied to any ganglioside to give derivatives which are useful in the present invention.

EXAMPLES

The present invention will now be described by reference to specific examples, but the invention is not to be construed as being limited thereto.

Unless otherwise specified, all percents, ratios, etc., are by weight.

Example 1

Synthesis of de-N-Acetyl $GM_3(D_1)$

Figure 2:
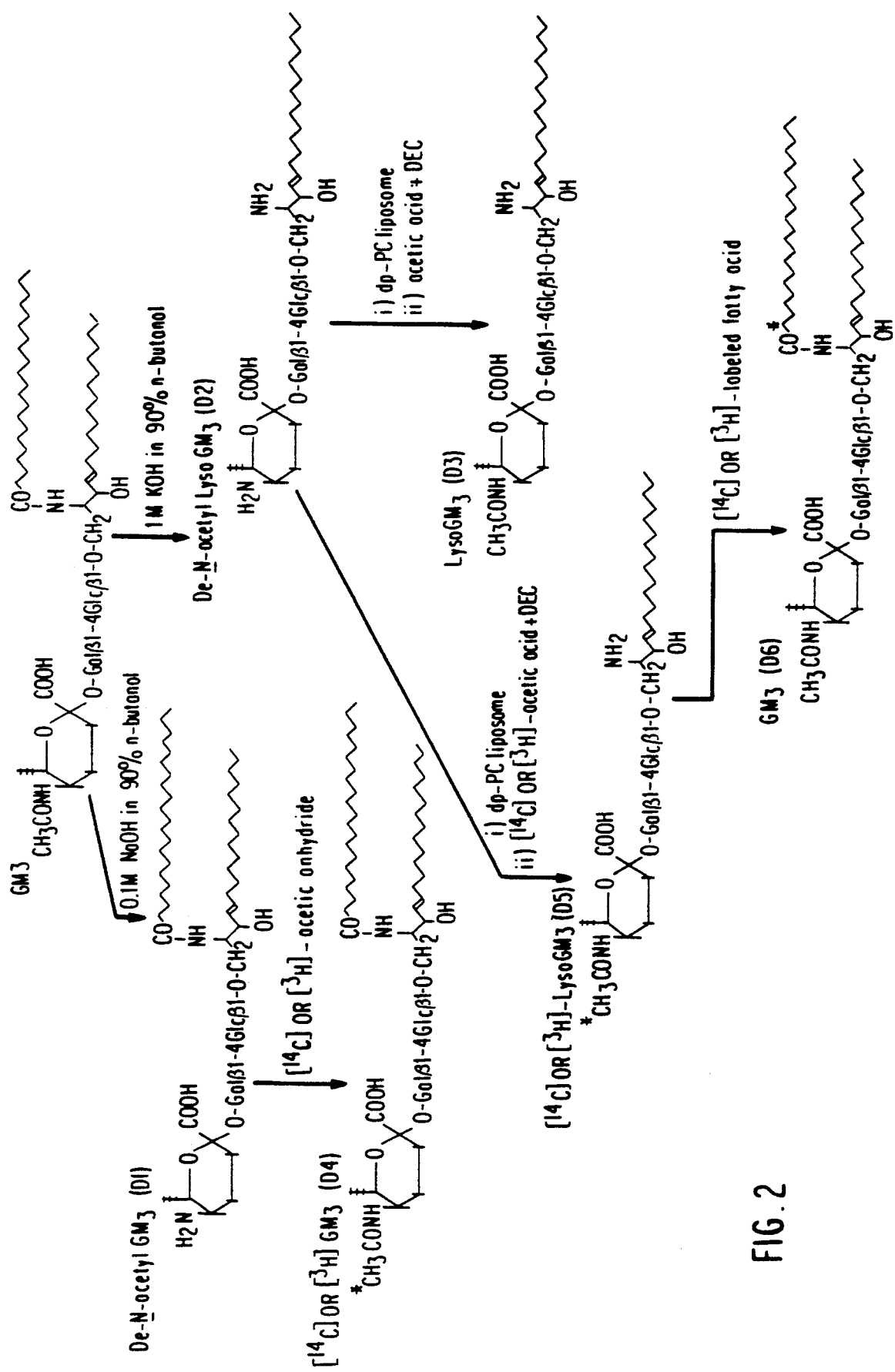
FIG. 2 is a schematic diagram of the various methods according to the present invention as described in the Examples with respect to the ganglioside $GM_3$, including a scheme for synthesis of de-N-acetyl-$GM_3$.

For clarity, reference can be made to FIG. 2 which is a diagram of the reaction schemes for producing the glycolipids of the present invention.

Figure 3:
FIG. 3 is a high-performance thin layer chromatography (HPTLC) pattern of the derivatives of $GM_3$ using chloroform-methanol-aqueous 0.2% $CaCl_2$ (5:4:1) and detection with resorcinol. $D_3$=lyso-$GM_3$. $D_1$=de-N-acetyl-$GM_3$, and $D_2$=de-N-acetyl-lyso-$GM_3$.

Isolation of $GM_3$ ganglioside—$GM_3$ containing N-acetyl-neuraminic acid was extracted from dog erythrocytes and purified by chromatography (R. K. Yu and R. W. Ledeen (1972) *J. Lipid Res.* 13, 680–686) on DEAE Sephadex followed by high-performance liquid chromatography on a column of Iatrobeads 6RS8010 in a 2-propanol-hexane-water system as previously described (K. Watanabe and Y. Arao (1981) *J. Lipid Res.* 22, 1020–1024). The behavior on high-performance thin-layer chromatography is shown in FIG. 3.

Preparation of de-N-acetyl-$GM_3$—On hydrolysis with 0.1M NaOH in aqueous 90% 1-butanol at 80° for 4 hours, the N-acetyl group of $GM_3$ sialic acid was preferentially hydrolyzed to give de-N-acetyl-$GM_3$, which has a free amino group at the sialic acid moiety of $GM_3$ (See FIG. 4)., as the main product ($\geq 70\%$). The hydrolysate in aqueous 1-butanol was neutralized with 12M HCl, concentrated to dryness, and a solution of the residue in water (6 ml) was passed through a column of $C_{18}$ silica (Bond Elut, Analytichem International, Oxnard, Calif.). After washing with water to eliminate salts, the lipids were diluted with methanol. The derivatives were finally purified by high-performance liquid chromatography. The behavior on high-performance thin-layer chromatography is shown in FIG. 3.

Example 2

Synthesis of N-[$^{14}$C]-Acetyl $GM_3(D_4)$

De-N-acetyl-$GM_3$ was N-acetylated with [$^{14}$C]-acetic anhydride in methanol containing 0.1M NaHCO$_3$ as follows.

Dried samples were dissolved in 50 μl of 0.5M NaHCO by stirring and heating at 60° C. Twenty-five μCi [$^{14}$C]-acetic anhydride (5.1 mCi/mmol) in 0.1 ml of methanol was added and the mixture was incubated for 1 hour at room temperature. After drying under a nitrogen stream, the reaction mixture was dissolved in distilled water and loaded on a $C_{18}$ silica gel column. Labeled glycolipid was eluted with chloroform:methanol (2:1, v/v) and analyzed by HPTLC (chloroform:methanol: 0.02% $CaCl_2$—2 $H_2O$, 60:40:9, v/v/v) through HPLC by Iatrobeads 6RS8010.

Example 3

Synthesis of Lyso $GM_3(D_3)$ $GM_3$ containing N-acetyl-neuraminic acid was extracted from dog erythrocytes and purified by chromatography as described in Example 1 above.

Preparation of de-N-acetyl-lyso-$GM_3$ ($D_2$)—De-N-acetyl-lyso-$GM_3$ is characterized by the absence of the N-acetyl group at the sialic acid moiety and the N-acyl group at the ceramide moiety of $GM_3$ (See FIG. 2).

In order to prepare de-N-acetyl-lyso-$GM_3$ a solution of $GM_3$ (6 μmol) in 1M KOH in aqueous 90% butanol (3 ml) was heated at 117° for 2 hours. Under these conditions, originally described by Taketomi and Yamakawa (T. Taketomi and T. Yamakawa (1963) *J. Biochem. (Tokyo)* 54, 444–451). more than 95% of the $GM_3$ was converted into de-N-acetyl-lyso-$GM_3$.

Figure 4:
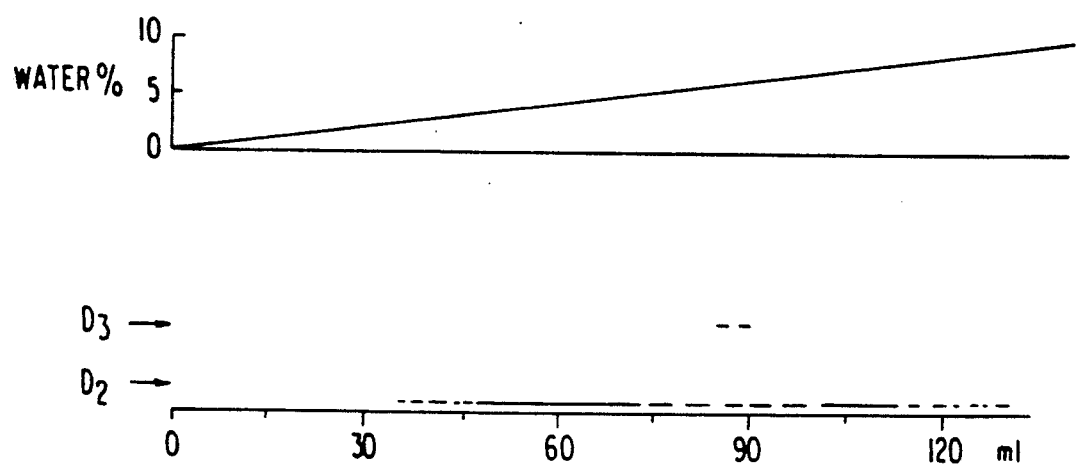
FIG. 4 is a high-performance thin-layer chromatography pattern of the products of carbodiimide-catalyzed N-acetylation of de-N-acetyl-lyso-$GM_3$ ($D_2$) in micellar dispersion.

The behavior on high-performance thin-layer chromatography and in high-performance liquid chromatography is shown in FIGS. 3 and 4, respectively.

Synthesis of lyso-GM$_3$ (D$_3$)—The neuraminic acid residue of de-N-acetyl-lyso-GM$_3$ was preferentially N-acetylated by protecting the amino group of the sphingosine by inserting the de-N-acetyl-lyso-GM$_3$ in a liposome of dpPC (dipalmotoylphosphatidylcholine, obtained from Sigma Chemical Co.).

De-N-acetyl-GM$_3$ (1 μmol) was dried together with dpPC (10 μmol). A solution of 20 mg of DEC (aminopropylethylcarbodiimide, obtained from Aldrich Chemical Co.) in water (1 ml) was added, and the lipids were resuspended by sonication with the needle probe of a sonicator (Braun-Sonic 1510) using 30 watts of power for about 5 minutes. The suspension was cooled to 4° and the N-acetylation reaction was initiated by adding 0.1M acetate buffer (0.2 ml. pH 5.2). After incubation for 24 hours at 4°, the reaction was stopped by the addition of ethanolamine (20 μmol) followed by chloroform-methanol (5 ml, 2:1). The lower phase was washed with the same volume of chloroform-methanol-water (3:47:48 v:v:v), and the combined upper phases were dried, resuspended in water, desalted by passage through a C$_{18}$ silica column and purified by HPLC to give lyso-GM$_3$ (70-80%). The behavior on high-performance thin layer chromatography and in high-performance liquid chromatography is shown in FIGS. 3 and 4, respectively.

Example 4

Characterization of GM$_3$ Derivatives D$_1$, D$_2$ and D$_3$

The derivatives were characterized by NMR spectroscopy and negative ion fast atom bombardment (f.a.b.) spectrometry. Solutions of the compound (400 μg) in Me$_2$SO-d$_6$-D$_2$O (98:2, 0.3 ml) were stored for 5 minutes to allow deuterium exchange of hydroxy and amino protons. Each solution was then lyophilized and a solution of the residue Me$_2$SO-d$_6$D$_2$O (98:2, 0.5 ml) was used immediately for NMR spectroscopy. $^1$H-NMR spectra were obtained at 35° with a Bruker WM-500 spectrometer equipped with an Aspect 2000 computer using quadrature detection, a spectral width of 5000 Hz over 16K data points, and a relaxation delay of 2 s. The number of transients collected varied from 200 to 500. Chemical shifts are referenced to the terminal methyl resonance(s), the shift of the resonance of which was assumed to be 0.85 p.p.m.

Figure 5:
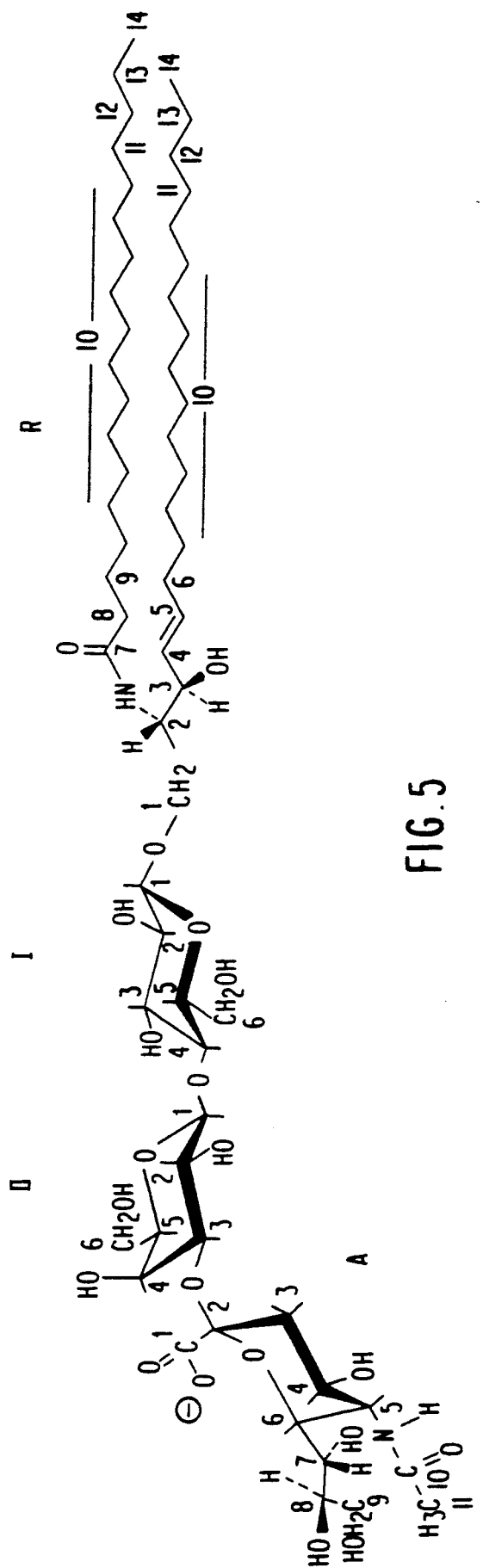
FIG. 5 is a proton labeling scheme for NMR analysis of $GM_3$.

The structure and proton labeling scheme for GM$_3$ de-N-acetyl-GM$_3$ (D$_1$), de-N-acetyl-lyso-GM$_3$ (D$_2$) and lyso-GM$_3$ (D$_3$) are shown in FIG. 5.

Negative ion f.a.b -mass spectrometry was performed using a JEOL HX-110 mass spectrometer/DA-5000 data system. Solutions of samples in methanol were transferred to a triethanolamine or glycerol matrix on the f.a.b. target and bombarded with a xenon beam. The acceleration voltage was 10 kV and the resolution was 3000. Data were acquired in the accumulation mode from 100-1500 a.m.u. (atomic mass units) with a scan slope of 1 min/decade. Each spectrum represents the accumulation of three scans. Sodium iodide in glycerol was used as the mass calibration standard.

FIGS. 6A, 6B, 6C and 6D show the $^1$H-NMR spectra of GM$_3$, D$_3$, D$_1$ and D$_2$, respectively, along with selected resonance assignments.

The spectrum of GM$_3$ (FIG. 6A) is identical to that previously reported (T. A. W. Koerner Jr., et al (1983) *Biochemistry* 22, 2676-2690) and the assignments follow those of these authors, except for the amide protons, which were not assigned (T. A. W. Koerner Jr., et al (1983) *Biochemistry* 22, 2676-2690). The amide assignments were made by comparison with the spectra of de-N-acetyl-GM$_3$ (D$_1$) and lyso-GM$_3$ (D$_3$), and agree with the assignments for GM$_3$ in Me$_2$SO-d$_6$ (deuterated dimethyl sulfoxide) at 35° (S. Gasa et al (1983) *J. Lipid Res.* 24, 174-182).

Of special note for the identification of GM$_3$ derivatives are the resonances for the cis olefinic protons of the unsaturated fatty acid (δ 5.3), the anomeric protons of glucose (I-1, δ 4.17) and galactose (II-1, δ 4.19), NAc of the sialic acid (A-11, δ 1.88), and the amide protons R-N and A-N (δ 7.45 and 7.98, respectively).

Figure 6B:
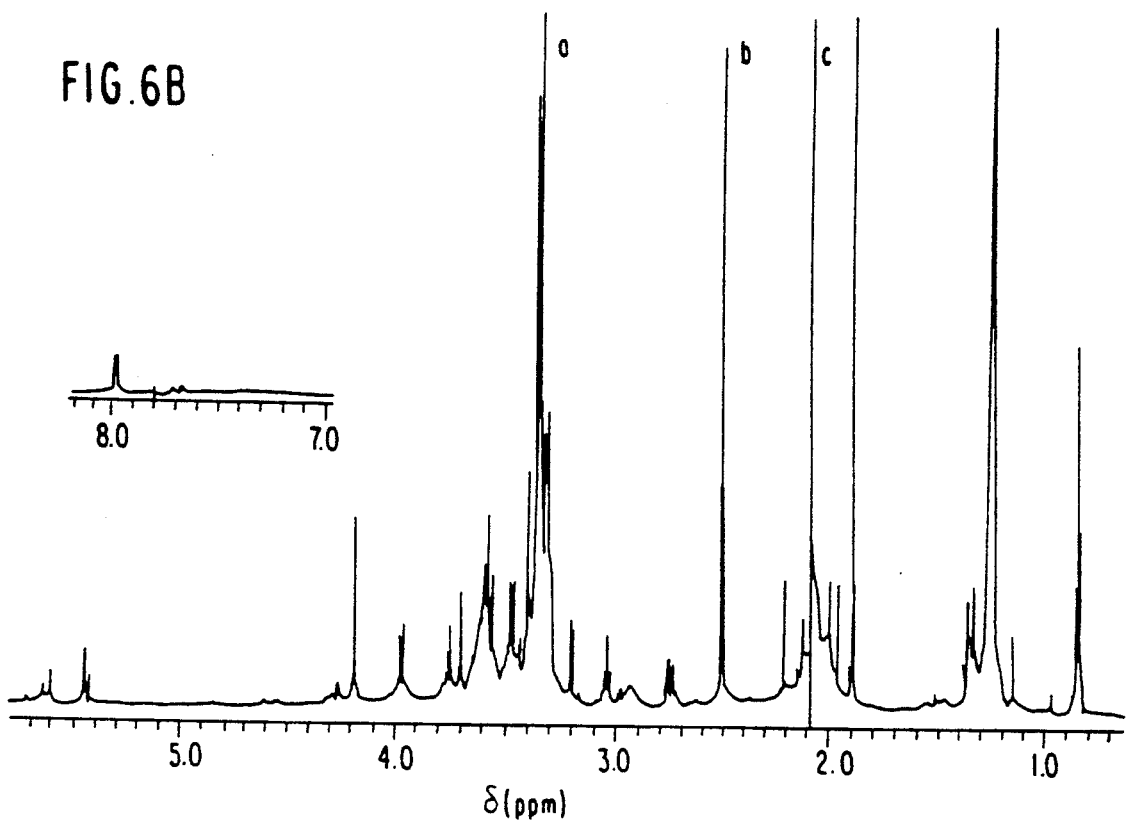
FIG. 6 shows resolution enhanced $^1$H-NMR spectra: (A) $GM_3$, (B) lyso-$GM_3$ ($D_3$), (C) de-N-acetyl-$GM_3$ ($D_1$) and (D) de-N-acetyl-lyso-$GM_3$ ($D_2$). The resonance assignments given in (A) follow those of Koerner et al (T. A. W. Koerner, Jr., et al (1983) *Biochemistry* 22, 2676-2690). The peaks a-c are due to HOD. $Me_2SO$, and acetone, respectively.
Figure 6A:
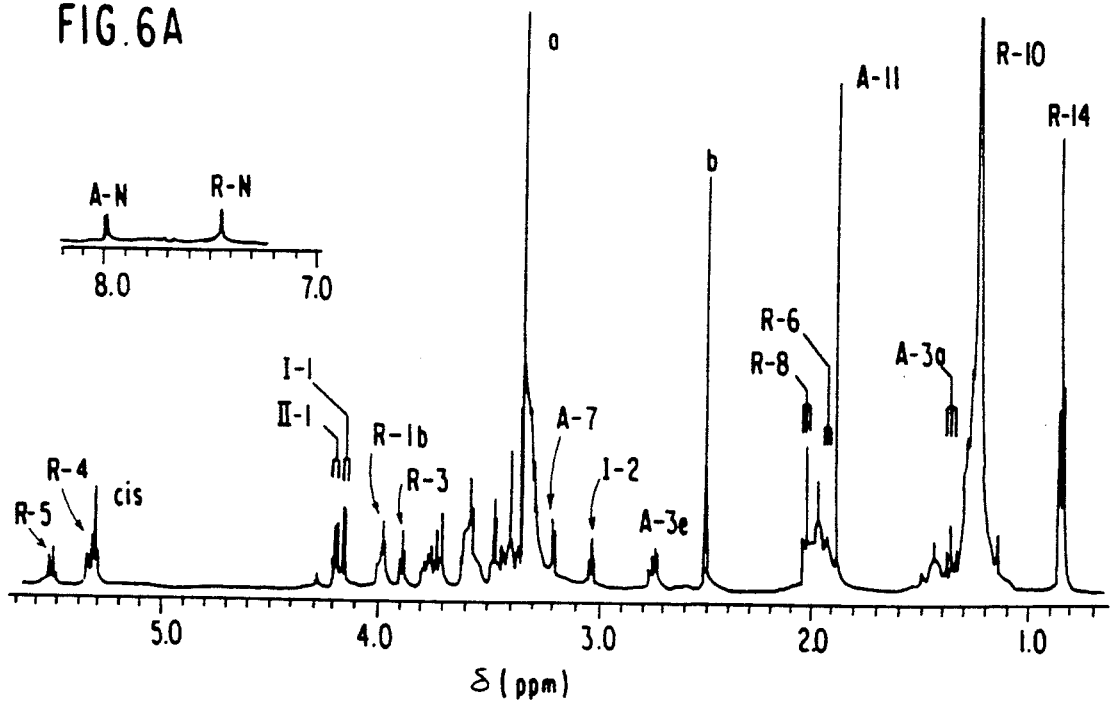

Comparison of the spectra of lyso-GM$_3$ (D$_3$) FIG. 6B) and GM$_3$ shows that the former lacks the resonances (δ 5.3) due to the cis olefinic protons of the unsaturated fatty acid and the amide proton (δ 7.45). Loss of the fatty acid from sphingosine was verified by integration of the methylene (R-10) and terminal U(R-14) resonances (δ 1.25 and 0.85, respectively). Another notable difference between the spectra of GM$_3$ and lyso-GM$_3$ is the down-field shift (0.032 p.p.m.) for the resonance of the glucose anomeric proton (I-1) in the spectrum of lyso-GM$_3$. This significant substituent effect is most likely caused by loss of the anisotropic shielding of the fatty acid carbonyl. The change in the chemical shift of the resonance of the glucose anomeric protein upon loss of the fatty acid implies a relatively close approach of the fatty acid carbonyl to the glucose anomeric proton in GM$_3$, and may have implications for the secondary structure of GM$_3$. Other differences between the spectra of FIGS. 6A and 6B are evident and are compatible with the proposed structure of lyso-GM$_3$; the sphingosine olefinic proton resonances R-4 and R-5 (δ 5.3 and 5.5, respectively) are shifted down-field in FIG. 6B compared to their positions in FIG. 6A. In addition, the multiplicities and chemical shifts of the resonances of the sphingosine protons R-1b and R-3 (δ 3.96 and 3.88, respectively) change upon loss of the fatty acid bound to sphingosine.

Figure 6C:
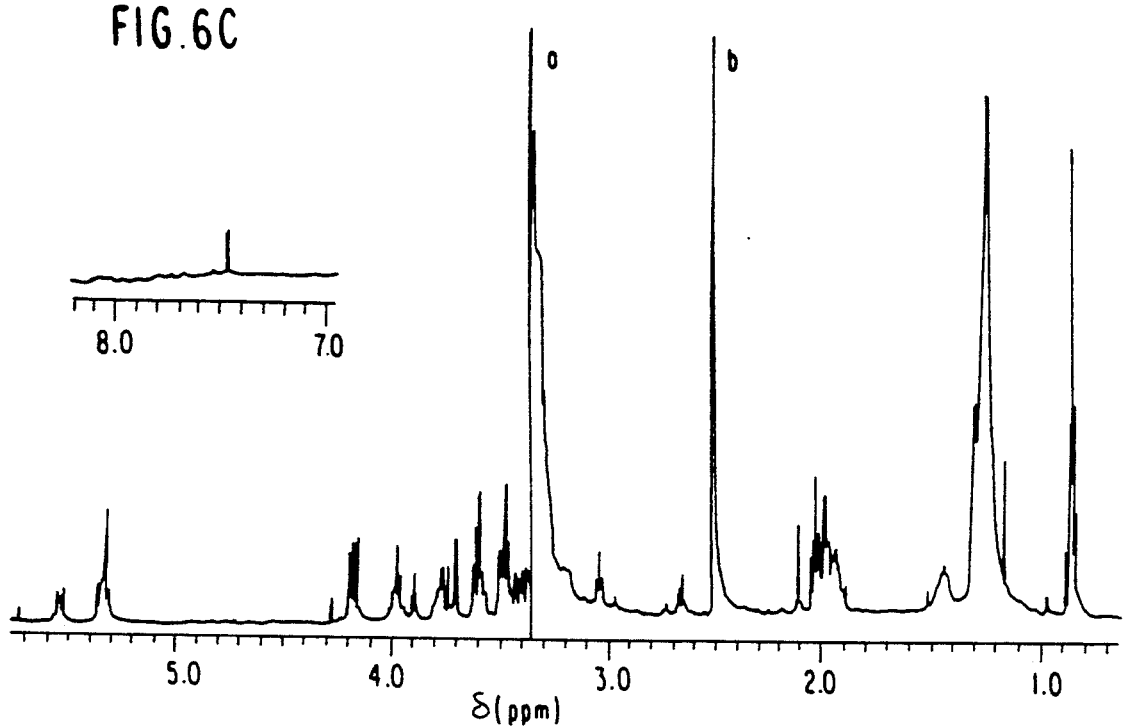

FIG. 6C shows the spectrum of de-N-acetyl-GM$_3$ (D$_1$) which differs from that of GM$_3$ by the absence of the resonances for the sialic acid acetamide methyl group (A-11, δ 1.89) and the sialic acid amide proton (A-N, δ 7.98). In addition, the resonance for sialic acid H-7, which appears at δ 3.1 in the spectrum of GM$_3$, moved down-field in the spectrum of de-N-acetyl-GM$_3$, whereas that of H-3e moved up-field (−0.1 p.p.m.). These shifts may be explained by loss of the anisotropic effect of the carbonyl of the acetamide group formerly bound to neuraminic acid.

Figure 6D:
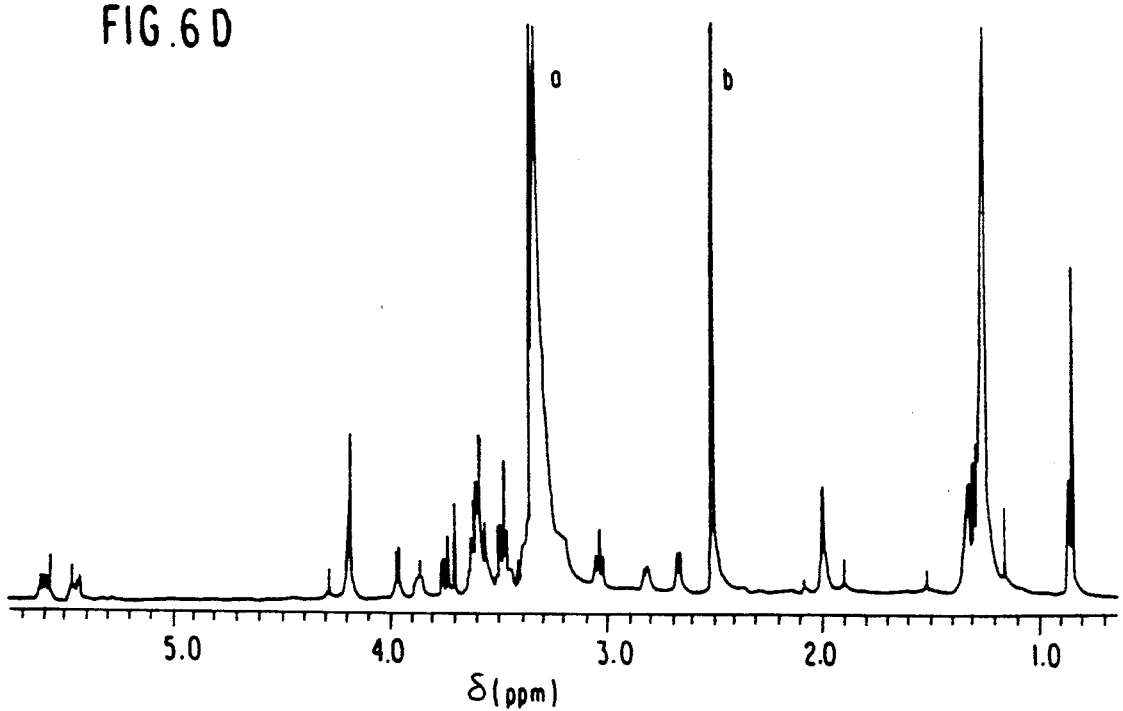
Figure 8:
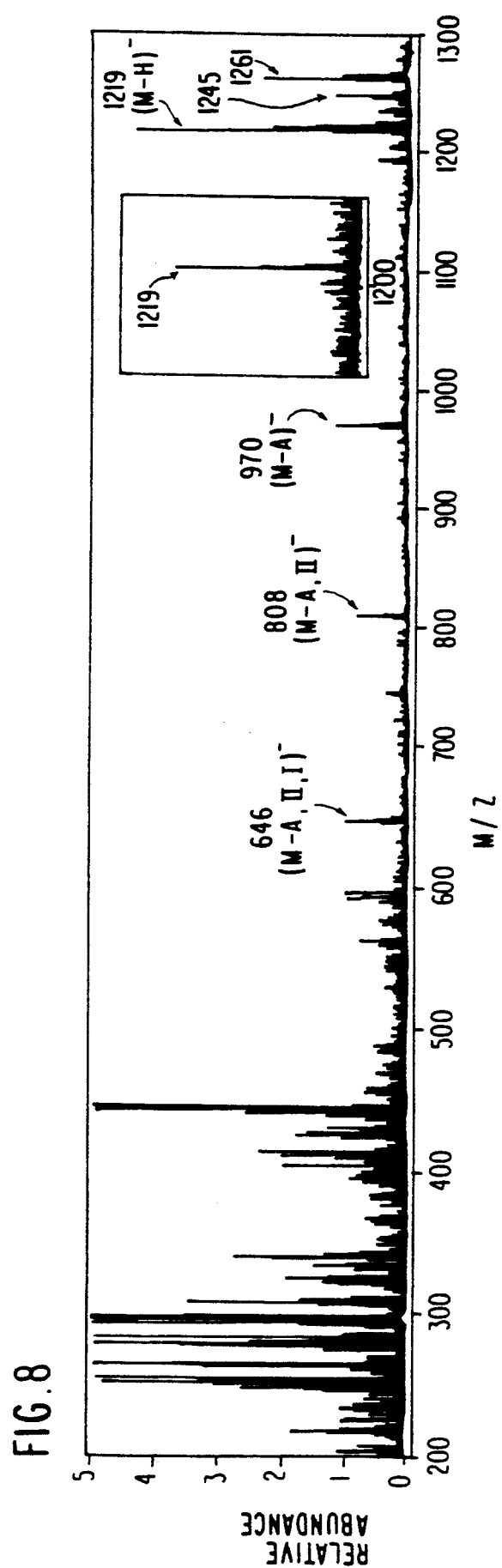
FIG. 8 is a negative ion f.a.b.-mass spectrum of de-N-acetyl-$GM_3$ ($D_1$) in a triethanolamine matrix. Inset: molecular ion region of spectrum in a glycerol matrix.

The spectrum of de-N-acetyl-lyso-GM$_3$ (D$_2$) appears in FIG. 6D. The spectrum of de-N-acetyl-lyso-GM$_3$ contains no resonance for NAc.

The major fragments observed in the mass spectra of GM$_3$ and D$_1$-D$_3$ obtained in both triethanolamine and glycerol matrices are summarized in Table I and the spectra are shown in FIGS. 7-10, respectively.

TABLE 1

Mass (m/z) of relevant fragments produced by negative ion f.a.b.-mass spectrometry of $GM_3$ and synthetic derivatives

```
      [M—A  [M—A,II  [M—A,II—I
Neu—O—Gal—O—Glc—O—CH2CHCHOHCH=CH(CH2)12CH3
 |              |
 NH             NH
 |              |
 R1             R2

A    II    I
```

| | $R_1$ | $R_2$ | M—H | M—A | M—A, II | M—A, II,I |
|---|---|---|---|---|---|---|
| $GM_3$ | $COCH_3$ | $COC_{23}H_{45}$ | 1261 | 970 | 808 | 646 |
| $D_1$ | H | $COC_{23}H_{45}$ | 1219 | 970 | 808 | 646 |
| $D_2$ | H | H | 871 | 622 | 460 | 298$^a$ |
| $D_3$ | $COCH_3$ | H | 913 | 622 | 460 | 298$^a$ |

$^a$Obscured by the triethanolamine matrix cluster ion at m/z 297.

The negative ion f.a.b.-mass spectrum of $GM_3$ in a triethanolamine matrix (FIG. 7A) was dominated by the pseudo-molecular ions, some fragmentation occurring through loss of sugar residues from the non-reducing end, with charge retention on the ceramide-containing portion of the molecule. The presence in canine erythrocyte $GM_3$ of ceramide composed almost exclusively of d18:1 sphingosine and 24:1 (+24:0) fatty acid, was indicated by the abundant ion at m/z 1261 (1263). The fragment expected from d18:1 sphingosine, at m/z 237, was not observed in the spectrum.

In the spectrum obtained using a glycerol matrix (FIG. 7B), the same ions were observed (m/z 1261, 970, 808, 646), along with a number of glycerol cluster ions $(nG-1)^-$. The spectra of the mono-de-N-acyl compounds lyso-$GM_3$ ($D_3$) and de-N-acetyl-$GM_3$ ($D_1$) in a triethanolamine matrix were characterized by the unexpected presence, in addition to the abundant pseudomolecular $(M-H)^-$ ions, of ions 26 and 42 a.m.u. higher in mass. Since the $(M-H+42)^-$ ions coincide with the mass of $(M-H)^-$ expected for other synthetic derivatives which are N-acetylated, this finding was first interpreted as an indication of mutual contamination. However, the preparation and purification schemes seemed to exclude this possibility and, in addition, the $^1$H-NMR spectra did not corroborate the presence of mixtures. Moreover, the production of $(M-H+26)^-$ ions could not be explained simply as due to impurities, nor could the similarities in the relative abundances of these molecular weight region clusters. Finally, the occurrence of a second set of higher mass ions $[(M-H+42+16)^-$ and $(M-H+42+42)^-]$ in the spectrum of de-N-acetyl-lyso-$GM_3$ ($D_2$) (discussed further below), which is deacylated at both nitrogens, seemed to indicate that the presence of these ions is related to the number of free amino functions in the molecule, and that they are the result of some reaction taking place during the bombardment process in a triethanolamine matrix. In order to assess this possibility spectra were acquired in another matrix, glycerol. The results appear to confirm this hypothesis, as well as the identity and purity of the synthetic ganglioside derivatives.

Figure 10:
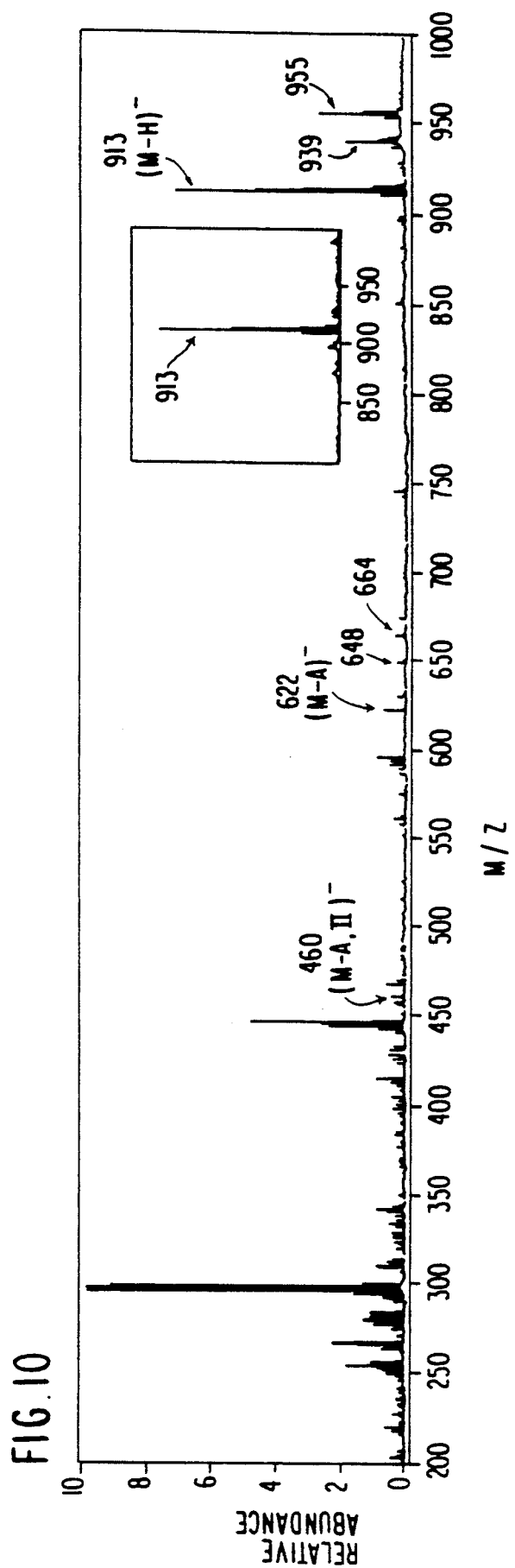
FIG. 10 is a negative ion f.a.b.-mass spectrum of lyso-$GM_3$ ($D_3$) in a triethanolamine matrix. Inset: molecular ion region of spectrum in a glycerol matrix.

Thus, whereas the spectrum of lyso-$GM_3$ ($D_3$) in a triethanolamine matrix (FIG. 10) contained abundant ions at m/z 913, these extra ions were absent in the spectrum obtained in a glycerol matrix (FIG. 10, inset). The spectrum of lyso-$GM_3$ in a triethanolamine matrix also contained ions corresponding to loss of NeuAc (m/z 622) and of NeuAc.Hex (m/z 460). The ion produced by loss of NeuAc and both hexoses, corresponding to (sphingosine-H), and expected at 298, was obscured by the large matrix cluster ion at m/z 297. Inspection of the spectrum of lyso-$GM_3$ in a triethanolamine matrix revealed ions at m/z 648 and 664, corresponding to the loss of NeuAc from the extra ions at m/z 939 and 955. respectively. This result might be expected from a chemical reaction involving a free amino group on sphingosine. The f.a.b.-mass spectrum for a glycerol matrix showed little useful fragmentation.

The de-N-acetylation of $GM_3$ NeuAc to produce de-N-acetyl-$GM_3$ ($D_1$) should reduce the mass of the pseudomolecular ions by 42 a.m.u. In the mass spectrum of de-N-acetyl-$GM_3$ in a triethanolamine matrix (FIG. 8), the expected predominant pseudomolecular ion was found at m/z 1219 (1221) for 24:1 (+24:0) fatty acid containing ceramides, accompanied, as for lyso $GM_3$, by associated $(M-H+26)^-$ and $(M-H+42)^-$ ions at m/z 1245 (1247) and 1261 (1263). As with lyso $GM_3$, the mass spectrum of de-N-acetyl-$GM_3$ in a glycerol matrix (FIG. 8, inset) exhibited only the pseudomolecular ions (m/z 1219, 1221), again with little useful fragmentation. The abundant fragment ions seen with the triethanolamine matrix (m/z 970, 972, 808, 810, 646, 648) were unaccompanied by additional higher mass clusters, since the terminal neuraminic acid possessing the free amino function was eliminated in the production of these fragments. The fact that the difference between $(M-H)^-$ and $(M-A)^-$ is 249 a.m.u., instead of 291 a.m.u. expected for loss of NeuAc, confined the missing 42 a.m.u. to that residue, confirming its de-N-acetylation.

In the spectrum of the di-de-N-acylated ganglioside. i.e., de-N-acetyl-lyso-$GM_3$ ($D_2$) taken in a triethanolamine matrix (FIG. 9A), the expected pseudomolecular ion at m/z 871 was accompanied by a series of abundant ions representing $(M-H+26)^-$, $(M-H+42)^-$, $(M-H+42+26)^-$, and $(M-H+42+42)^-$. A less abundant ion, representing $(M-H+26+26)^-$, could also be detected. With a glycerol matrix, only the pseudomolecular ion could be seen (FIG. 9B). The ion representing elimination of $NeuNH_2$ was present in the spectra for both the triethanolamine and glycerol matrices at m/z 622, and in former only was this accompanied by the higher mass ions m/z 648 and 664, as found for lyso-$GM_3$. The fragment representing loss of $NeuNH_2.Hex$ (m/z 460) was detectable for the triethanolamine matrix, but its presence in the glycerol matrix was obscured by a matrix cluster ion at m/z 459.

Example 5

Demonstration of de-N-acetyl-$GM_3$ in Various Cell Lines and Tissues

Preparation of glycolipids and modified glycolipids $GM_3$ and de-N-acetyl-$GM_3$ were prepared as described in Example 1. $GM_1$ and $GM_2$, used as standards, were prepared by extraction from bovine brain by standard methods, followed by extraction with organic solvent, Folch's solvent partition, DEAE sephedex chromatography, HPLC, etc. as described in, for example, *Sphingolipid Biochemistry*, Plenum Press, S. Hakomori (1983). De-N-acetyl-$GM_1$ was prepared by a method analogous to that set forth in Example 1, except that the starting material was extracted from bovine brain.

Cell Culture

The A431 human vulvar epidermoid carcinoma cell line (Fabricant, R. N. et al (1977) *Proc. Natl. Acad. Sci. USA* 74, 565-569). Swiss 3T3 mouse fibroblast cell line, and B16 mouse melanoma cell line were used in this study. The medium used for the culture was basal medium (a mixture of DME and F-12 in the volume ratio of 1:1). Cells were grown in basal medium supplemented with 5% calf serum. Cells were also grown in serum-free media supplemented with 5 $\mu$g/ml insulin. 5 $\mu$g/ml of transferrin. 5 ng/ml sodium selenite, and 100 $\mu$g/ml fatty acid-free BSA including 1% linoleic acid (serum-free defined DME/F-12 medium). For the culture of Swiss 3T3 cells in serum-free medium. 10 ng/ml EGF and 10 ng/ml PDGF were added to serum-free defined DME/F-12 medium. To culture Swiss T3 cells and B16 cells in serum-free medium, plates were coated with fibronectin in advance by incubating 40 $\mu$l of 10 $\mu$g/ml fibronectin in PBS for 2 hours at room temperature.

Culture of B16 melanoma cells grown in mice as in vivo tumor

B16 melanoma cells were also prepared by growing them in syngeneric mice as in vivo tumors by methods well known in the art.

Sources of tissue samples

Normal rat brain tissue samples were obtained from laboratory rats (Wistar Laboratories, Philadelphia, Pa.).

Normal rat liver tissue samples were obtained from laboratory rats (Wistar Laboratories, Philadelphia, Pa.).

Human colonic cancer tissue was obtained from surgical samples.

Ganglioside extraction from cells and tissues

Cultured cells were harvested using a rubber policeman, and pelleted by centrifugation. Cells from tissues were passed through a wire mesh and also pelleted by centrifugation. The cell pellets were extracted with chloroform:methanol (2:1, v/v), followed by three partitions with $H_2O$ according to the modified method of Folch (Folch-Pi, J., et al (1951) *J. Biol. Chem.* 191, 819-831). The Folch upper phases were combined, evaporated to a small volume, and freed from salt with a $C_{18}$ silica gel column (Kundu, S. K. an Suzuki, A. (1985) *J. Chromatogr.* 224, 249-256) followed by DEAE-Sephadex chromatography (Ledeen, R. W. and Yu, R. K. (1982) *Meth. Enzymol.* 83, 139-191 and Nores, G. and Caputto, R. (1984) *J. Neurochem.* 42, 1205-1211). The monosialoganglioside fraction eluted with chloroform:methanol:0.08M ammonium formate (30:60:8, v/v/v) was desalted with a $C_{18}$ silica gel column and evaporated to dryness in a rotary evaporator. The dried material was applied on a porous silica gel column of Iatrobeads 6RS8010, which was equilibrated with n-propanol-15% aqueous ammonium hydroxide (75:15, v/v), and eluted with a gradient from the same solvent to n-propanol-15% aqueous ammonium hydroxide (75:25 v/v) during 200 minutes in Varian 500 HPLC equipment. The eluates were collected over a fraction collector (2 ml/fraction), and each fraction was analyzed on HPTLC. Under these conditions, $GM_3$ and de-N-acetyl-$GM_3$ were eluted in that order and clearly separated without overlap.

[$^{14}$C]-acetylation of gangliosides

For each cell line or tissue, the fraction containing de-N-acetyl-$GM_3$ was N-acetylated with [$^{14}$C]-acetic anhydride in methanol containing 0.1M $NaHCO_3$ as follows.

Dried samples were dissolved in 50 $\mu$l of 0.5M $NaHCO_3$ by stirring and heating at 60° C. Twenty-five $\mu$Ci $^{14}$C-acetic anhydride (5.1 mCi/mmol) in 0.1 ml of hexane was added and incubated for 1 hour at room temperature. After drying under a nitrogen stream, the reaction mixture was dissolved in distilled water and loaded on a $C_{18}$ silica gel column. Labeled glycolipid was eluted with chloroform:methanol (2:1, v/v) and analyzed by HPTLC (chloroform:methanol:0.02% $CaCl_2$—2 $H_2O$. 60:40:9, v/v/v) through HPLC by Iatrobeads 6RS8010.

Additionally, the de-N-acetyl-$GM_3$ fraction from half of 25 g of pelleted cells or tissue was N-[$^{14}$C]-acetylated and separated on HPTLC (chloroform:methanol:0.02% $CaCl_2$—$2H_2O$, 50:40:10, v/v/v), and followed by autoradiography.

Preparation of monoclonal antibody DH5, which specifically reacts with de-N-acetyl-$GM_3$ De-N-acetyl-$GM_3$, prepared as described in Example 1, was adsorbed on acid-treated *Salmonella minnesotae*. Alternatively, the compound was lactonized by being dissolved in chloroform:methanol:12N HCl (60:30:4.5 v/v/v) and allowed to stand for 18 hours (Nores, G., et al (1987) *J. Immunol.* 139, 3171-3176). The hydrochloric acid was evaporated under a nitrogen stream, and the residue was dissolved in water, adsorbed on acid-treated *S. minnesotae*, and used as immunogen according to the method previously described (Nores, G., et al (1987) *J. Immunol.* 139, 3171-3176 and Young, W. W. Jr., et al (1979) *J. Exp. Med.* 150, 1008-1019). The immunization protocol and procedures for preparing, selecting and cloning of monoclonal antibodies were also conducted according to previously described known methods (Nores. G., et al (1987) *J. Immunol* 139, 3171-3176 and Young. W. W. Jr., et al (1979) *J. Exp. Med.* 150. 1008-1019).

The hybridoma secreted $IgG_3$ antibody DH5, which specifically reacts with de-N-acetyl-$GM_3$ and neuraminyl 2→3 paragloboside ($IV^3NeuNH_2nLc_4$), but does not react with $GM_3$ or any other ganglioside, including $GM_1$ containing neuraminic acid ($III^3NeUNH_2Gg4$).

The specificity of this monoclonal antibody was determined by solid-phase radioimmunoassay by a procedure previously described (Kannagi, R., et al (1983) *Cancer Res.* 43, 4997-5005).

Briefly, 20 pmole/well of de-N-acetyl-$GM_3$, $GM_3$, de-N-acetyl-$GM_1$, $GM_1$, neuraminylparagloboside (prepared by de-N-acetylation of sialylparagloboside which was obtained from human erythrocytes (*Sphingolipid Biochemistry*, Plenum Press, S. Hakomori, (1983)), or sialylparagloboside (isolated from human erythrocytes (*Sphingolipid Biochemistry*, Plenum Press, S. Hakomori, (1983)) with 50 ng/well phosphatidylcholine and 30 ng/well cholesterol in ethanol were dried onto 96 well plastic plates. The wells were blocked with 5% BSA in PBS for 2 hours and reacted with various concentrations (see FIG. 11) of monoclonal antibody DH5 for 2 hours at room temperature. Bound antibody was detected using rabbit anti-mouse IgG followed by $^{125}$I- protein A. The radioactivity of each well was counted with a gamma counter.

Figure 11:
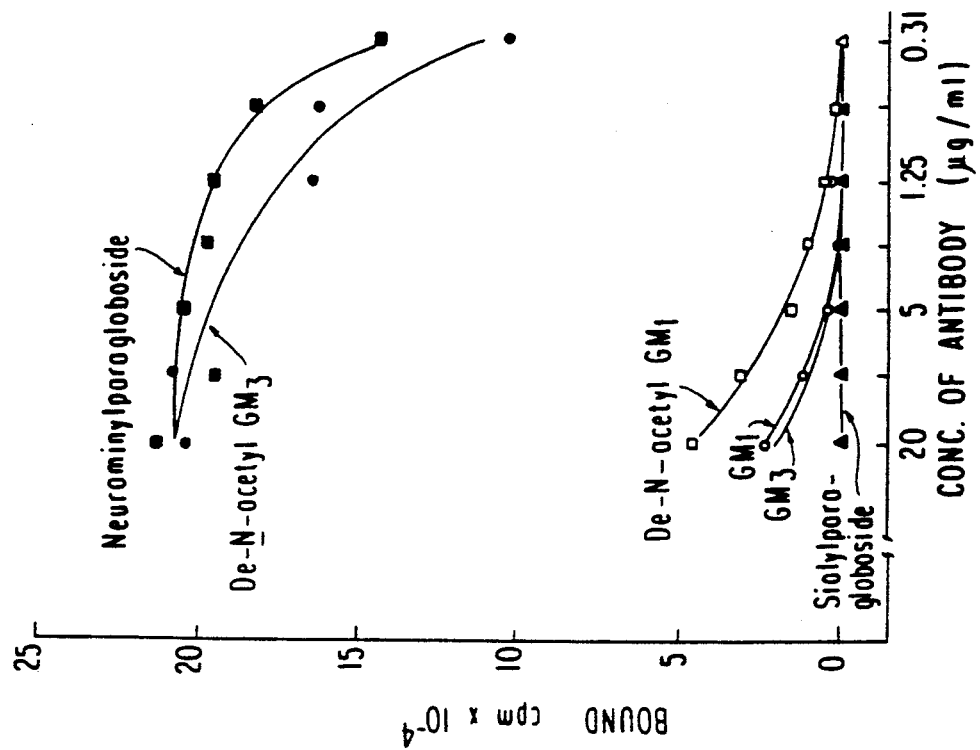
FIG. 11 is a graph showing the reactivity of DH5 monoclonal antibody with various glycolipids determined by solid-phase radioimmunoassay. De-N-acetyl-$GM_3$ (closed circles): $GM_3$ (open upside down triangles): $GM_1$ containing neuraminic acid (open squares, indicated as de-N-acetyl-$GM_1$ in the figure); $GM_1$ (open circles); neuraminylparagloboside (closed squares): sialylparagloboside (closed triangles).

The results are shown in FIG. 11. As can be seen from the results, the only ganglioside to which monoclonal antibody DH5 is specific is de-N-acetyl-$GM_3$.

Analogous methods can be used to produce monoclonal antibodies specific to other gangliosides containing de-N-acetyl-sialic acid.

TLC Immunostaining

TLC Immunostaining was carried out as described by Magnani et al (Magnani, J. L. et al (1980) Anal. Biochem. 109, 399–402).

Specifically, the monosialoganglioside fraction from a 100 mg cell or tissue pellet was spotted on TLC plates for chromatography using a solvent system of chloroform:methanol:water (50:40:10, v/v/v) containing 0.05% $CaCl_2$. TLC plates were coated with plastic, blocked with 5% BSA in PBS, and reacted with culture supernatant of monoclonal antibody DH5-producing hybridomas for 2 hours at room temperature. Bound antibody was detected using a rabbit anti-mouse IgG antibody followed by $^{125}$I-protein A, and tested by autoradiography.

Figure 12A:
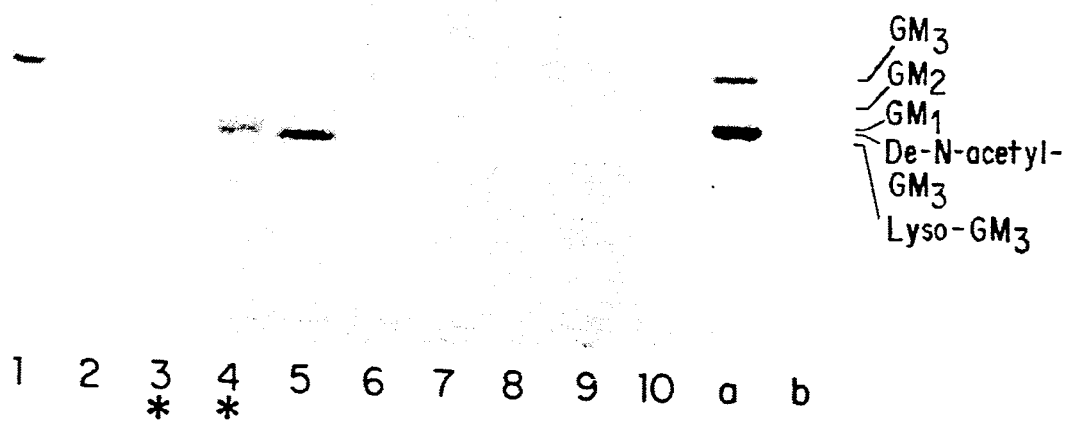
FIG. 12 shows a separation pattern of the de-N-acetyl-$GM_3$ fraction, its thin-layer chromatography (TLC) immunostaining, and its detection as N-[$^{14}$C]-acetyl-$GM_3$ from A431 cells. Panel A: orcinol/$H_2SO_4$ staining. Lanes 1-10 show the separation pattern of standard $GM_3$ and de-N-acetyl-$GM_3$ on HPTLC (chloroform:methanol:0.02% $CaCl_2$—$2H_2O$, 50:40:10) through high-performance liquid chromatography (HPLC) by Iatrobeads 6RS8010. De-N-acetyl-$GM_3$ fractions are indicated by an asterisk at the bottom. Lane a: standard $GM_1$, $GM_2$, and $GM_3$: and lane b, standard de-N-acetyl-$GM_3$ (upper band). Panel B shows an immunostaining pattern of HPTLC plate, using monoclonal $IgG_3$ antibody DH5 directed to de-N-acetyl-$GM_3$ and its lactone. In lanes 1-10. separated monoganglioside fractions from A431 cell extracts through HPLC under the same conditions are shown in panel A; lane c shows standard de-N-acetyl-$GM_3$; and lane d, standard $GM_1$, $GM_2$, $GM_3$. Positively stained de-N-acetyl-$GM_3$ bands are indicated by arrows. Panel C shows the N-[$^{14}$C]-acetylated de-N-acetyl-$GM_3$ fraction from A431 cells separated on HPTLC chloroform:methanol:0.02% $CaCl_2$—$2H_2O$, 50:40:10), and followed by autoradiography. The position of N-[$^{14}$C]-acetylated $GM_3$ is indicated by the arrows. Lane 1 shows N-[$^{14}$C]-acetylated standard de-N-acetyl-GM₃; and lane 2, N-[¹⁴C]-acetylated de-N-acetyl-GM₃ fraction from A431 cells.
Figure 12B:
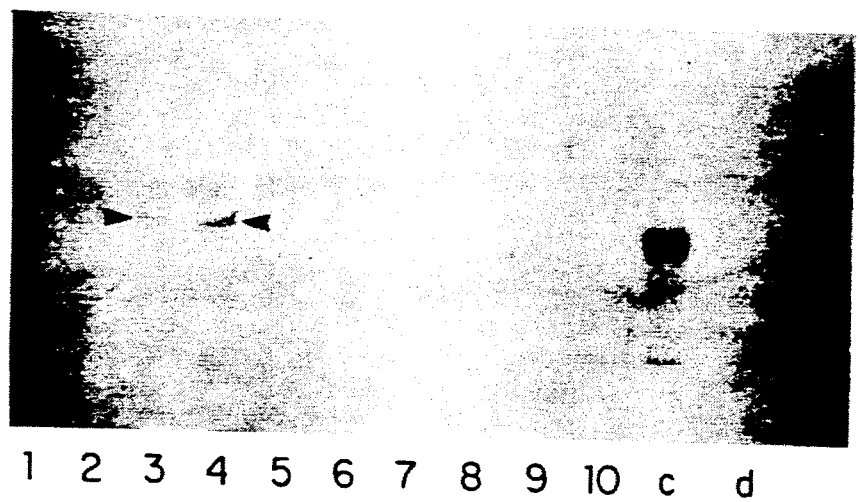
Figure 12C:

The results are shown in FIGS. 12 and 13.

FIG. 12, panel A shows the separation pattern (lanes 1-10) of orcinol/$H_2SO_4$ stained (Sphingolipid Biochemistry, Plenum Press, S. Hakomori, (1983)) monosialoganglioside fractions from A431 cells separated by chromatography on a DEAE-Sephadex A25 column followed by HPLC on a porous silica gel column through Iatrobeads 6RS8010. The de-N-acetyl-$GM_3$ containing fractions are indicated by an asterisk at the bottom. Lanes a and b are standards.

FIG. 12, panel B shows the separation pattern (lanes 1-10) of immunostained (with monoclonal $IgG_3$ antibody DH5 monoganglioside fractions from A431 cells separated as described for panel A. The de-N-acetyl-$GM_3$ containing fractions are indicated by arrows. Lane c is a standard consisting of de-N-acetyl-$GM_3$ and lane d is a standard consisting of $GM_1$, $GM_2$ and $GM_3$.

FIG. 12, panel C shows N-[$^{14}$C]-acetylated de-N-acetyl-$GM_3$ fraction separation on HPTLC and followed by autoradiography. The position of N-[$^{14}$C]-acetylated $GM_3$ is indicated by the arrows. Lane 1 is an N-[$^{14}$C]-acetylated de-N-acetyl-$GM_3$ standard and lane 2 is the N-[$^{14}$C]-acetylated de-N-$GM_3$ fraction from A431 cells.

The results in FIG. 12 clearly indicate that A431 cells contain de-N-acetyl-$GM_3$.

FIG. 13 shows TLC staining of the monosialoganglioside fraction of various cell lines and tissues. Panel A shows resorcinol/HCl staining (Sphingolipid Biochemistry, Plenum Press, S. Hakomori, (1983)) and panel B shows immunostaining with the monoclonal antibody DH5.

Lane 1 is a standard with $GM_3$, $GM_1$, de-N-acetyl-$GM_3$ and de-N-acetyl-$GM_1$ ($GM_1$ containing neuraminic acid). Lanes 2, 3, 4, 5 and 6 are fractions from B16 melanoma tumor grown in vivo, B16 cells cultured in vitro, Swiss 3T3 cells cultured in vitro, rat liver and rat brain, respectively.

From these results it is seen that B16 melanoma cells that were grown in mice as an in vivo tumor or cultured in vitro contain de-N-acetyl-$GM_3$, whereas normal rat brain and normal 3T3 cells do not contain de-N-acetyl-$GM_3$, and normal rat liver only contains a small amount, in relative terms, of de-N-acetyl-$GM_3$.

Further, a significant quantity of de-N-acetyl-$GM_3$ was found in human colonic cancer cells when treated according to the above methods.

In the above experiments, any possibility for artificial production of de-N-acetyl $GM_3$ was eliminated by the absence of de-N-acetyl $GM_3$ when [$^3$H]-palmetoyl $GM_3$ was processed by the same procedure for preparation of the monosialoganglioside fraction.

Example 6

Effect of de-N-acetyl-$GM_3$ Tyrosine Kinase Activity of EGF Receptor

Membrane preparation and receptor kinase activity

The cell membrane fraction of A431 cells cultured as described in Example 5 was prepared according to the method described previously (Hanai, N. et al (1987) Biochem. Biophys. Res. Commun. 147, 127–134). Briefly, confluent cell cultures in 150 mm plastic dishes were scraped, pelleted in PBS (800×g), and resuspended in 7 ml of 20 mM HEPES buffer (pH 7.4), 1 mM EGTA, 0.5 mM phenylmethylsulfonyl fluoride in 250 mM sucrose, homogenized in a Dounce homogenizer with a tight-fitting pestle (Weaton Scientific, Millerville, N.J.), and centrifuged at 3000×g for 10 minutes. The supernatant fraction was centrifuged at 100,000×g for 1 hour, and the pellet was suspended in 300 μl of 200 mM HEPES buffer (pH 7.4), aliquoted, and frozen in a liquid nitrogen tank. The phosphorylation of membrane proteins, particularly EGF receptor, was performed as previously described (Bremer, E., et al (1986) J. Biol. Chem. 261, 2434–2440) with a few modifications. Briefly, cell membranes were incubated in the buffer (20 mM HEPES, pH 7.4, 1 mM $MnCl_2$, 10 μM $ZnCl_2$, 30 μM $NaCO_3$) including 0.33 μM EGF (receptor grade: Collaborative Research, Waltham, Mass.) plus 1.5 μM carrier BSA and various concentrations of Triton X-100 (high purity detergent, Pierce. Ill.) in the presence or absence of gangliosides for 10 minutes at 25° C. The reaction was started by the addition of 1.0 μM or 10 μM [gamma-$^{32}$P]ATP (10 μCi) for 10 min at 0° C. The total reaction volume was 50 μl, and the amount of membrane protein was 25 μg. The reactions were terminated by addition of 50 μl of Laemmli's sample buffer (Laemmli, U. K. (1970) Nature 227, 680–685). Aliquots of the incubation mixture were subjected to 8% SDS-polyacrylamide gel electrophoresis. The gel was washed with 1M NaOH for 15 min at 25° C., then treated with 1M NaOH for 1 hour at 40° C. to reduce serine or threonine O-phosphate (Cheng, Y. S. E. and Chen. B. (1981) Proc. Natl. Acad. Sci. USA 78, 2388–2392) and dried, followed by visualization by autoradiography. The region containing the EGF receptor (170 Kd band) was excised from the gel, and the $^{32}$P activity was determined by a liquid scintillation counter. Amino acid phosphate analysis was performed on the EGF receptor fraction excised from the gel according to the method previously described (Cooper, J. A. et al (1983) Meth. Enzymol. 99, 387–402).

Figure 14:
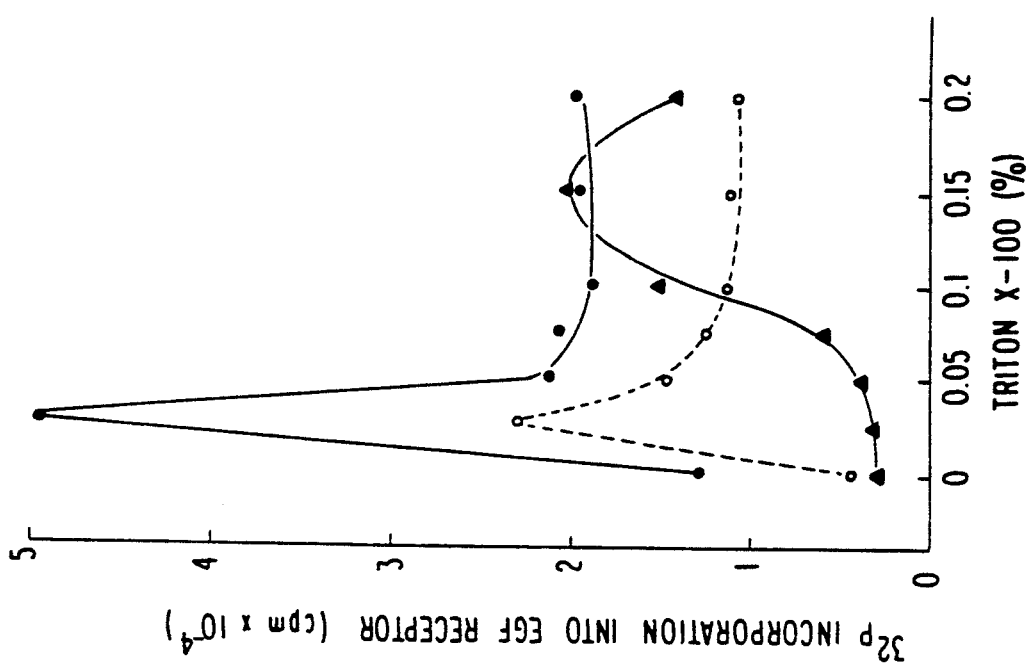
FIG. 14 is a graph showing EGF receptor kinase activity of A431 cell membranes: dependence on Triton X-100 concentration and on GM$_3$ and de-N-acetyl-GM$_3$ Open circles indicate control without ganglioside addition: closed triangles, with 500 μM GM$_3$; and closed circles, with 250 μM de-N-acetyl-GM$_3$.
Figure 16A:
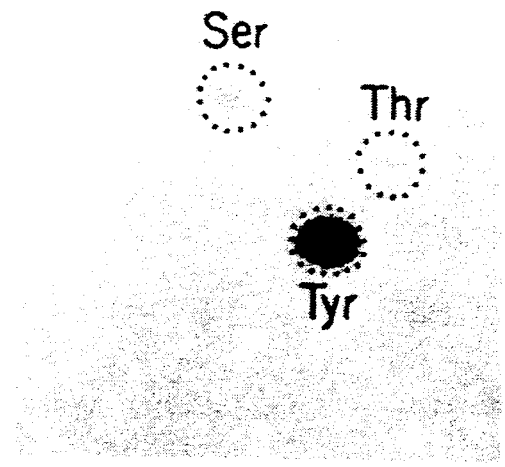
FIG. 16 is an autoradiograph of two-dimensional thin-layer electrophoresis of amino acid phosphates from a hydrolysate of EGF receptor band excised from a gel region containing EGF receptor. Panel A: only EGF; panel B: EGF and de-N-acetyl-GM$_3$. Ser: serine phosphate. Thr: threonine phosphate, Tyr: tyrosine phosphase.
Figure 16B:
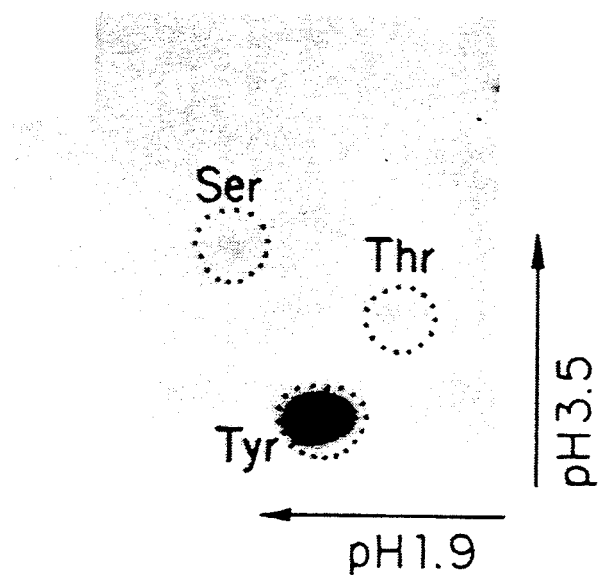

The results are shown in FIGS. 14, 15 and 16.

FIG. 14 shows the dependence of EGF receptor kinase activity of A431 cell membranes on Triton X-100 concentration. The open circles represent control samples wherein no ganglioside was added to the assay; the closed triangles represent samples wherein $GM_3$ was added; and the closed circles represent samples wherein de-N-acetyl-$GM_3$ was added.

The results show that EGF-dependent receptor kinase activity was strongly enhanced by addition of de-N-acetyl-GM$_3$ with or without Triton X-100, although the receptor kinase activity is closely correlated with the concentration of this detergent in vitro assay. EGF-dependent kinase activity was enhanced in control cells at very low detergent concentration (0.025%). In the presence of de-N-acetyl-GM$_3$, the receptor kinase activity was several-fold higher at this low detergent concentration, and was always 2-4 fold higher regardless of detergent concentration in the assay system. When Triton X-100 concentration was lower than 0.1%, GM$_3$ inhibited the kinase activity strongly.

FIG. 15 shows the effect of de-N-acetyl-GM$_3$ on in vitro phosphorylation of EGF receptor depending on ganglioside concentration keeping the EGF concentration constant at 0.33 μM (Panel A) and EGF concentration keeping the de-N-acetyl-GM$_3$ concentration constant at 500 μM (Panel B). In all cases, the Triton X-100 concentration was 0.025%. The closed circles represent de-N-acetyl-GM$_3$; the open circles represent a control without ganglioside addition; and the (X) represents no EGF.

The results indicate that the promoting effect of de-N-acetyl-GM$_3$ on EGF-dependent receptor kinase activity increases when the concentration of de-N-acetyl-GM$_3$ in A431 cell membranes is increased (FIG. 15, panel A). The enhancing effect of de-N-acetyl-GM$_3$ on EGF receptor kinase activity was observed even without addition of EGF, although it was more obvious when EGF concentration was increased up to 0.1-0.2 μM (FIG. 15, panel B).

FIG. 16 shows the phosphoamino acid pattern in a hydrolysate of the EGF receptor band taken from the gel region containing the EGF receptor. The gel region was excised and hydrolyzed with 5.7M HCl at 110° C. for 1 hour. At the end of the hydrolysis, the mixture was lyophilized and spotted onto a 20×20-cm cellulose thin-layer plate. Two-dimensional thin-layer electrophoresis was carried out at pH 1.9 and at pH 3.5.

Panel A shows the results where the sample contained only EGF and Panel B shows the results where the sample contained EGF and de-N-acetyl-GM$_3$.

The results show that when phosphoamino acid analysis was performed on the hydrolysate of the EGF receptor in the presence or absence of de-N-acetyl-phosphorylation GM$_3$, enhanced phosphorylation was found corresponding only to tyrosine phosphate, but not serine or threonine phosphate.

Example 7

Effect of de-N-acetyl-GM$_3$ and GM$_3$ on Cell Growth

A431 cells Swiss 3T3 cells, and B16 cells were seeded into 96-well plates in serum-free medium as described in Example 5 at a density of $0.4 \times 10^4$ cells/well. On the third day of culture. 10 μM de-N-acetyl-GM$_3$ was added to A431 cells; 50 μM de-N-acetyl-GM$_3$ or 50 μM GM$_3$ was added to Swiss 3T3 cells; 50 μM de-N-acetyl-GM$_3$ or 50 μM GM$_3$ was added to B16 cells. For a control, no ganglioside was added.

Each day the number of cells was counted and the average of 4 determinations plus or minus standard error was taken as the number of cells.

Purified gangliosides were added to the cell culture medium as follows. Ganglioside in chloroform:methanol solution was transferred to a glass test tube, evaporated under a nitrogen stream, dissolved in culture medium at the indicated concentration, sonicated, and passed through a 0.2 μ sterilizing filter.

The results are shown in FIG. 17 where Panel A represents A431 cells, panel B represents Swiss 3T3 cells and panel C represents B16 cells. Closed circles represent de-N-acetyl-GM$_3$ addition; closed triangles represent GM$_3$ addition; and open circles represent no ganglioside addition.

The results show that A431 cell growth was significantly enhanced when cells were cultured in medium to which de-N-acetyl-GM$_3$ was exogenously added (FIG. 17, panel A) as compared with cells cultured in medium only. A growth promoting effect by de-N-acetyl-GM$_3$ was most pronounced with 3T3 cells, in which GM$_3$ was strongly growth-inhibitory (FIG. 17, panel B). Growth of B16 melanoma cells was strongly inhibited by GM$_3$ but not affected by de-N-acetyl-GM$_3$ (FIG. 7, panel C).

While the invention has been described in detail and with reference to specific embodiments thereof, it will be apparent to one skilled in the art that various changes and modifications can be made therein without departing from the spirit and scope thereof.

What is claimed is:

1. Substantially pure de-N-acetyl GM$_3$.
2. A medicament for stimulating growth of human and animal cells comprising:
   (1) a cell growth stimulating amount of de-N-acetyl GM$_3$, or pharmaceutically acceptable salts thereof; and
   (2) a pharmaceutically acceptable carrier, diluent or excipient.
3. The medicament of claim 2, wherein said cells are mammalian cells.
4. The medicament of claim 2, wherein said cells are cells involved in wound healing.
5. The medicament of claim 2, wherein said medicament promotes wound healing.
6. The medicament of claim 2, wherein said cells have insulin-dependent growth.

* * * * *